(12) United States Patent
Dorian et al.

(10) Patent No.: US 9,345,869 B2
(45) Date of Patent: May 24, 2016

(54) OXYGEN DIFFUSIVE WOUND DRESSINGS AND METHODS OF MANUFACTURING AND USE

(71) Applicants: Randy Dorian, San Diego, CA (US); Alexander B. Izvorski, San Francisco, CA (US); Richard W. Storrs, Berkeley, CA (US)

(72) Inventors: Randy Dorian, San Diego, CA (US); Alexander B. Izvorski, San Francisco, CA (US); Richard W. Storrs, Berkeley, CA (US)

(73) Assignee: Owl Manor Medical, LLC, New Orleans, LA (US)

( * ) Notice: Subject to any disclaimer, the term of this patent is extended or adjusted under 35 U.S.C. 154(b) by 494 days.

(21) Appl. No.: 13/650,003

(22) Filed: Oct. 11, 2012

(65) Prior Publication Data

US 2014/0107562 A1     Apr. 17, 2014

(51) Int. Cl.
| | |
|---|---|
| *A61F 13/00* | (2006.01) |
| *A61M 37/00* | (2006.01) |
| *A61M 35/00* | (2006.01) |
| *A61M 1/00* | (2006.01) |

(52) U.S. Cl.
CPC .......... *A61M 37/00* (2013.01); *A61F 13/00021* (2013.01); *A61F 13/00068* (2013.01); *A61M 1/0088* (2013.01); *A61M 35/00* (2013.01)

(58) Field of Classification Search
CPC . A61F 13/00; A61F 13/1302; A61F 13/0203; A61L 15/425; A61L 15/28; A61L 15/325; A61M 35/00; A61M 37/00
USPC .............................. 602/41–43, 46, 47, 48, 52; 604/304–308, 289–291
See application file for complete search history.

(56) References Cited

U.S. PATENT DOCUMENTS

| | | | | |
|---|---|---|---|---|
| 2,340,142 | A | * | 1/1944 | Rauner .......................... 604/306 |
| 4,641,643 | A | | 2/1987 | Greer |
| 4,803,078 | A | | 2/1989 | Sakai |
| 4,909,243 | A | | 3/1990 | Frank et al. |
| 5,340,363 | A | * | 8/1994 | Fabo .............................. 604/304 |
| 5,512,041 | A | | 4/1996 | Bogart |
| 5,738,642 | A | | 4/1998 | Heinecke et al. |
| 6,051,747 | A | * | 4/2000 | Lindqvist ................ A61F 13/02 602/41 |
| 6,077,526 | A | | 6/2000 | Scully et al. |
| 6,221,460 | B1 | | 4/2001 | Weber et al. |
| 7,381,859 | B2 | | 6/2008 | Hunt et al. |
| 2002/0161317 | A1 | | 10/2002 | Risk et al. |

(Continued)

FOREIGN PATENT DOCUMENTS

| | | |
|---|---|---|
| FR | 2647337 A1 * | 11/1990 |
| WO | WO 2014/058532 | 4/2014 |

OTHER PUBLICATIONS

Paul Sharma et al., Chitosan and Alginate Wound Dressings: A Short Review, Trends Biomater., Artif. Organs, vol. 18(1), pp. 18-23, 2004.

(Continued)

*Primary Examiner* — Kim Lewis
(74) *Attorney, Agent, or Firm* — Levine Bagade Han LLP

(57) ABSTRACT

Oxygen diffusive wound dressings and methods of manufacturing and use are described herein. The wound dressing may generally provide a ready supply of oxygen to a wound being treated via one or more oxygen conduits which are designed to pass oxygen from ambient air or other oxygen reservoirs into proximity to the wound, and may also provide for exudate removal through transecting channels in fluid communication with both the wound surface and a hydrophilic absorbent material.

98 Claims, 23 Drawing Sheets

(56) References Cited

U.S. PATENT DOCUMENTS

| | | |
|---|---|---|
| 2003/0148118 A1* | 8/2003 | Omori et al. .......... 428/457 |
| 2004/0126413 A1 | 7/2004 | Sigurjonsson et al. |
| 2007/0225663 A1 | 9/2007 | Watt et al. |
| 2009/0082740 A1 | 3/2009 | Lockwood et al. |
| 2012/0078154 A1 | 3/2012 | Pigg et al. |
| 2012/0220973 A1 | 8/2012 | Chan et al. |
| 2014/0107561 A1 | 4/2014 | Dorian |

OTHER PUBLICATIONS

NHS Purchasing and Supply Agency, Centre for Evidence-based Purchasing, Buyers Guide, Advanced wound dressings, CEP08038, 90 pages, Oct. 2008.

S. Schreml et al., Oxygen in Acute Chronic Wound Healing, The British Journal of Dermatology, vol. 163(2): 257-268, 12 pages, Sep. 15, 2010, 2010 Blackwell Publishing, http://www.medscape.com/viewarticle/727614_print.

Chandan K. San, Wound Healing Essentials: Let There Be Oxygen, Wound Repair Regin. vol. 17(1): 1-18., 30 pages, Feb. 2009, The Comprehensive Wound Center, Departments of Surgery and David Heart and Lung Research Institute, The Ohio State University Medical Center, Columbus OH.

Aicken et al., Tielle Plus with LiquaLock does more with optimal MVTR, 2 pages, Systagenix Wound Management 2011.

Breda Cullen et al., An evaluation of wound dressings to manage wound exudate and conform to the wound bed, 1 page, Systagenix Wound Management, Gargrave, UK.

Sarah Aickin et al., Evaluating Current in-vitro Assays for Assessing Fluid Handling Properties of Dressings and their Clinical Relevance, 1 page, Systagenix Wound Management, Gargrave, UK.

Steven Foster et al., The Evaluation of Fluid Retention in Foam Dressing, Systagenix Wound Management, Test methods for primary wound dressings part 1: Aspects of Absorbency, Gargave, UK, 1 page, 2002.

Sally-Anne Stephens et al., Evaluation of the Free Passage of Fluid Through a new Non-Adhering Silicone Wound Contact Layer, 1 page, Systagenix Wound, Gargrave, UK.

* cited by examiner

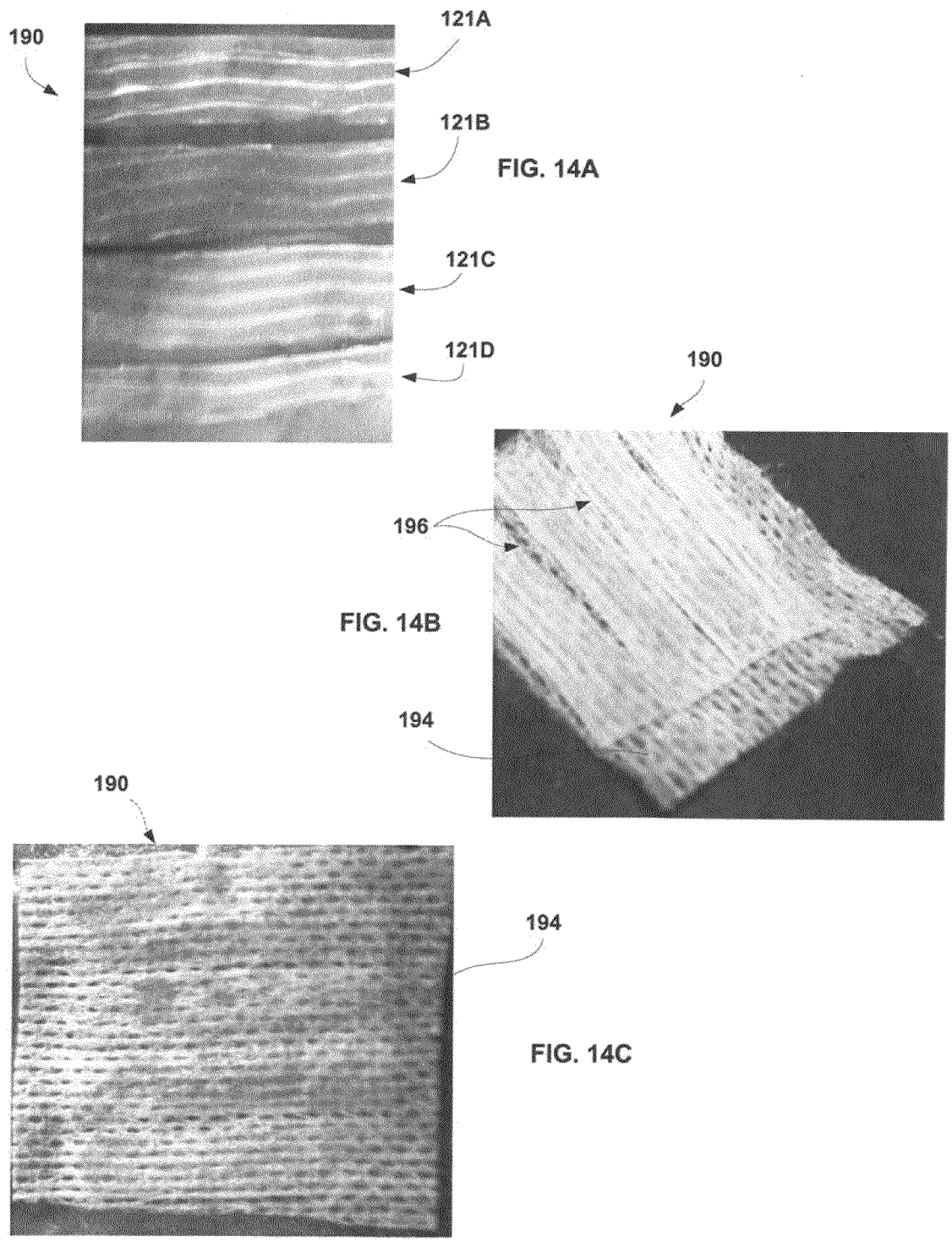

OXYGEN DIFFUSIVE WOUND DRESSINGS AND METHODS OF MANUFACTURING AND USE

FIELD OF THE INVENTION

The present invention relates to wound dressing apparatus and methods of their manufacturing and use. More particularly, the present invention relates to wound dressings that allow for the oxygenation and prevention of dehydration of wounds while removing exudate from the wounds and methods of their use.

BACKGROUND OF THE INVENTION

To facilitate the healing of wounds, the wound environment needs to be conducive to cell survival and proliferation. If the wound becomes dehydrated or if a pool of exudate develops above or within the wound, oxygen diffusion to or through the wound becomes impeded and the cells become hypoxic, which impairs their function (for example, the antimicrobial activity of neutrophils or the production of collagen by fibroblasts). Under sustained hypoxic or anoxic conditions the cells may die. This is especially true if the wound has impaired vascular delivery of oxygen from the native blood vessels. Dressings which are used to simply cover wounds typically absorb at least a thin layer of exudate (e.g., more than a couple hundred microns of exudate within the dressing). If the exudate and/or if the dressing material itself limits oxygen permeation to the wound, the covered cells may die and impede wound healing. As the cells die, they release cytotoxic factors which cause additional cells to die, potentially leading to a downward spiral of cell death.

Wound dressings generally cover a wound and limit dehydration but also restrict oxygen availability to the wound, which leads to cells becoming anoxic and dying due to the limited oxygen supply. Cellular preparations such as platelet rich plasma gels improve wound healing, and providing oxygen from outside the wound may improve their effectiveness.

For aggressively weeping wounds, dressings used sometimes rely on evaporation to remove excess water from the exudate and wound site; however, this has the undesirable effect of concentrating toxic factors (e.g., metalloproteases) in the exudate and may worsen conditions. Moreover, excess evaporation may also lead to wound dehydration which may further worsen the environment for wound healing. Dried exudate can form a crust with abrasive properties, further impeding healing.

In some treatments, wet gauze or hydrogel dressings are used to maintain a moist wound environment. In other situations hyperbaric oxygen treatments are used to oxygenate wounds. Other treatments for oxygenating wounds have used glucose and glucose oxidase to generate oxygen in situ or electrolysis of water in situ to generate oxygen. Other designs have actively delivered oxygen gas via a cannula under conventional dressings.

Yet other treatments have delivered peroxide rather than oxygen to wound sites where the peroxide is converted to oxygen in situ by native catalase or by, e.g., manganese dioxide.

Additional treatments have utilized films as dressings, e.g., polyurethane films, which include a stored reservoir of oxygen for application to the wound. Such reservoirs require replenishment. Absorbent materials such as polyHEMA hydrogel beads are sometimes poured directly into a wound. Foreign materials poured into a wound may trap layers of exudate, water, or debris after becoming saturated, limiting oxygen diffusion through the interstitial spaces. Moreover, depending on the molecular weight exclusion profile of the absorbent material, debris and toxic high molecular weight constituents of the exudate may become concentrated as water is absorbed into the material.

Accordingly, there is a need for a wound dressing which is able to maintain consistent high levels of oxygen permeability, prevent dehydration, and accommodate potentially copious volumes of exudate.

SUMMARY OF THE INVENTION

Wound dressings which maintain a high availability of oxygen to a wound and which also provide for uninterrupted exudate removal may utilize one or more oxygen conduits which are designed to pass oxygen from ambient air or other oxygen source into proximity to the wound where the oxygen may diffuse directly to the wound.

Generally, such a wound dressing may comprise a hydrophilic absorbent material (e.g., sponge, foam, absorbent hydrogel, etc.) a hydrophilic absorbent material envelope which defines an open area for contacting a wound site and which at least partially encloses the hydrophilic absorbent material, and at least one oxygen conductive conduit with an oxygen-diffusive coating, wherein the at least one conduit is positioned to extend exposed along the open area and adjacent to the hydrophilic absorbent material, and wherein the at least one conduit has at least one portion further exposed to a reservoir or source of oxygen to serve as a conduit for oxygen to the wound surface. Such a reservoir may be ambient air, compressed gas mixtures containing oxygen, oxygen generating chemical cells or highly oxygenated fluids such as perfluorocarbons. The hydrophilic absorbent material may be surrounded by an envelope which at least partially encloses the hydrophilic absorbent material, and defines an open area for contacting a wound site and which may impede evaporation of fluid from said hydrophilic absorbent material. Such a wound dressing may be applied to a wound site by placing the open area upon the wound site such that the at least one conduit is in contact against the wound site, and oxygen can diffuse from the at least one conduit and through the oxygen-diffusive coating to the wound site.

Additionally, the wound dressing may be formed through various manufacturing processes. One variation may generally comprise passing a length of multifilament fiber through a coating solution such that the fiber is coated via the solution while maintaining the openness of the internal interfilament spaces, arranging lengths of the coated fiber to align in parallel, woven, knit or otherwise arranged such that a coated fiber array is formed, securing the coated fiber array via one or more space-filling adhesive stripes placed transversely relative to a length of the coated fiber, positioning the coated fiber array over the open area of a hydrophilic absorbent material envelope and a hydrophilic absorbent material such that the hydrophilic absorbent material is positioned at a distance from the open area, and securing the hydrophilic absorbent material envelope such that the coated fiber array and hydrophilic absorbent material are sealed therein. The coating material and filament material may be hydrophobic to minimize condensation of water vapor diffusing through the coating, which could result in occlusion of the open interfilament spaces and a diminution of lateral oxygen diffusion along the length of the fiber.

The wound dressing may comprise a plurality of coated fibers, e.g., multifilament fibers or threads made from materials such as polypropylene or polyethersulfone, which may be coated with an oxygen diffusive material which may also be hydrophobic such as a thin silicone coating (e.g., low-viscosity acetoxy-cure silicone) or a microperforated hydrophobic coating whereby surface tension effects prevent aqueous liquid from traversing the perforations over the exterior of the fibers. In coating the fiber exterior, the fibers may be optionally first wetted with a liquid such as water or ethanol or isopropanol or mixtures thereof (such as 30% to 70% isopropanol) to prevent the coating solution from wicking into and between the filaments. Once the coating has been placed over the fiber, the liquid may evaporate ensuring that the conduits between the filaments are open for oxygen passage.

The coated fibers may also range in size and construction, e.g., about 40 to 2000 micron diameter threads or more particularly about 80 to 260 micron diameter threads with anywhere from 2 to several thousand filaments or more particularly a few to several filaments per fiber (such as 6 to 8 filaments). These fibers may be aligned adjacent and parallel to one another along the wound dressing and a hydrophilic absorbent material may be positioned over at least a portion of the fibers such that the hydrophilic absorbent material is optionally positioned at a distance from the wound when in use. Because the hydrophilic absorbent material is separated from the wound by the fibers and optionally the hydrophilic absorbent material envelope the hydrophilic absorbent material does not directly contact the wound and hence will not irritate or become engrafted into the wound.

The hydrophilic absorbent material may comprise any number of hydrophilic absorbent materials that freely allows for the absorption of large molecules and particulates such that there are no concentration effects on particulates or macromolecular toxic factors. For particular applications, where the benefit of increased concentration of beneficial factors present in the exudate (e.g., wound healing promoters) may outweigh the deleterious impact of toxic factor concentration, it may be desirable to optionally choose a hydrophilic absorbent material (e.g., a hydrogel such as polyacrylamide or dextranomer hydrogels) which will lead to an increase in concentration of macromolecular constituents of the exudate. The hydrophilic absorbent material may also inhibit or prevent gel polarization or fouling at the surface of the hydrophilic absorbent material. The hydrophilic absorbent material may be coated or otherwise covered by a film or membrane envelope (e.g., silicone, PVC, polyester, polyamide, or any other material which exhibits a low water vapor permeability) which coats or covers the faces of the hydrophilic absorbent material contiguous with the ambient environment. The hydrophilic absorbent material envelope may be hermetically sealed to help maintain a sterile environment at the wound site. While the hydrophilic absorbent material envelope may help to prevent excessive evaporation, the hydrophilic absorbent material envelope may be optionally removed or breached to encourage evaporation or removal of accumulated wound exudate, if so desired. One or more openings or ports in the hydrophilic absorbent material envelope may allow for the removal of accumulated exudate when the hydrophilic absorbent material becomes saturated and for the addition of fluids (optionally with drugs or other additives). The optional feature of being able to remove excess accumulated exudate through an access port permits the dressing to function indefinitely, obviating the need to periodically remove and replace the dressing when it becomes saturated with fluid, thereby saving labor and expense and limiting trauma to the wound site. Alternatively the hydrophilic absorbent material may be reversibly affixed to the dressing allowing removal and replacement when it becomes saturated with exudate.

The hydrophilic absorbent material and hydrophobic material envelope may be comprised of an absorbent wound dressing applied over an oxygen conductive assembly in contact with the wound, wherein a portion of the oxygen conductive assembly is in contact with air.

The hydrophilic absorbent material may be pre-moistened with saline solution or any number of agents (e.g., colloidal silver or other antimicrobial solutions, epinephrine, coagulants, anticoagulants, wound-healing promoters, inflammation inhibitors, wetting agents, etc.) either in the original package or added directly to the hydrophilic absorbent material prior to or after application of the dressing to the wound. Prior to application of the dressing to the wound, the wound site may be debrided (if necessary or desired) and an antimicrobial agent, such as colloidal silver or iodine preparations), may be applied directly to the wound. The dressing may then be placed upon the wound. The dressing may also be applied to wounds to enhance the benefits of, e.g., platelet gel, plasma concentrate, white cells, stem cells, skin grafts, growth factors, etc. which may be administered to the wound prior to application of the dressing. Preventing dehydration and maintaining high oxygen availability may be advantageous for such treatments.

With the hydrophilic absorbent material situated, the coated fibers (or other air conduits) may extend beyond the hydrophilic absorbent material longitudinally and/or laterally to form a border surrounding the hydrophilic absorbent material or they may be wrapped over the top of the dressing. The portion of the coated fibers extending beyond the open, wound contacting area may form an antenna for absorbing oxygen from the ambient air and may be coated or the gaps between adjacent coated fibers may be otherwise filled with an oxygen permeable material, e.g., silicone, and the underside of the border may have an adhesive formed thereupon such that when the dressing is placed over the wound, an open area exposing the coated fibers may be placed into direct contact against the wound. The adhesive border may encircle the wound such that any exudate from the wound is prevented or inhibited from wicking laterally. Instead, the exudate may wick between and through the gaps defined between the coated fibers along the open area within the coated fiber array and directly into the hydrophilic absorbent material where it may be retained by the hydrophilic absorbent material envelope.

With the coated fibers extending beyond the enveloped hydrophilic absorbent material, at least one of the terminal ends of the fibers may be left with open terminal ends along either or both ends of the dressing extending through the border. The open terminal ends of the fibers may provide openings for the additional entry of ambient air for passage through the length of the fibers. Thus, while the coated fibers form oxygen conduits where oxygen in the ambient air or other oxygen source may pass or conduct through the coated fibers (from the coated fiber terminal ends as well as through diffusion through the oxygen permeable coating) and further diffuse directly through the silicone coating and into the wound site, exudate may be prevented from entering into and fouling the coated fibers by their coating as the exudate passes into the hydrophilic absorbent material. In alternative variations, the conduits may be formed as hollow conduits or passages for allowing the passage of air or other oxygen source through with no multifilament fibers or threads. Such hollow conduits or passages may be used within any of the embodiments described herein.

Gaps between the coated fibers may allow conduction of wound exudate away from the wound surface into the hydrophilic absorbent material. The coated fibers may be bonded to one another by space-filling or adhering (e.g., silicone) stripes which are formed transversely to the coated fibers and which also provide for a smooth wound contacting surface and also prevent fluid accumulation between the coated fibers adjacent to the wound within the stripe coated areas. These transversely coated areas may be sufficiently wide while still allowing for sufficient removal of exudate through the intervening spaces to prevent any excessive exudate pooling as the width and spacing of these transversely stripes may affect how far the exudate travels to find a path from the wound surface and to the hydrophilic absorbent material.

While the coated fibers may directly contact the underlying wound, an optional membrane, e.g., track-etched polycarbonate or microperforated polymer film, may be interposed over the open area for contacting the wound. In the event that a membrane is used, such a membrane may be relatively thin and may further prevent adherence to the wound. Optional hydrophilic channels may extend from the membrane and through the coated fibers to the overlying hydrophilic absorbent material to allow for the conduction of exudate or infusion of various agents or drugs. The membrane may resist adhering to or integrating with the wound.

Optionally, an array of vertically oriented conduits (e.g., hollow air-filled tubes or channels, sealed at their termini to exclude exudate or fluid from the ambient environment from entering and flooding) may extend through the hydrophilic absorbent material to bring oxygen from above to the underlying wound-contacting membrane surface. The inner walls of said tubes or conduits may be hydrophobic to prevent water vapor condensation. To maximize uniformity of oxygen supply to the tissue, the conduits may be small and closely spaced. The hydrophilic absorbent material and dressing may be varied in size depending upon the size of the wound to be treated. Alternatively, the dressing may be formed into any number of standard uniform sizes.

One or more hydrophilic fibers or wicking material may be interspersed between the coated fibers within the open area of the coated fiber array to conduct exudate away from the wound. The number or amount and positioning of the hydrophilic fibers or material may be varied in various patterns, e.g., oxygen-conducting coated fibers may be interspersed between every two wicking fibers or so on, or they may be omitted completely. Moreover, the diameter of the wicking fibers, e.g., 700 microns, may be similar or identical to the diameter of the coated fibers although the diameters may also be varied depending upon the desired wicking properties. The outer surfaces of the coated fibers may be rendered hydrophobic, e.g., by surface modification chemistry, to promote conduction of exudate from the wound site to the hydrophilic absorbent material.

Another alternative may use individual fibers positioned in a transverse orientation relative to one another. A first set of fibers oriented parallel to one another may be laid atop a second set of fibers which are also parallel to one another such that the first and second set are transverse to one another. Alternatively, the crossing fibers may be interwoven with respect to one another and in other alternatives the crossing fibers may be orientated at some other angle rather than being orthogonal, e.g., 45 degrees relative to one another. The combined thickness of the crossing fibers may still be less than 1 mm.

Yet another variation may utilize a silicone contact film having one or more ridges or notches formed over its surface on the opposite side of the wound contact surface and including an upper film adhered and sealed to the ridges, forming an array of open conduits within a sealed envelope. These ridges or notches may be formed as ridges, undulations, tapered protrusions, or any other projections which extend between the two films to form lateral conduits for oxygen diffusion to the wound contact surface. One or more through-holes may be defined to extend in a direction normal to the surface for allowing any exudate to flow from the wound and to the hydrophilic absorbent material positioned above the contact film. A second film may be laid atop the contact film where the second film may define one or more through-holes that correspond to first film through-holes. With the second film positioned atop contact film, the open channels formed by the ridges or notches between the upper and lower films may function as the oxygen conduits where the oxygen may then diffuse through the contact film and into the underlying wound. Through-channels for wound exudate may be formed in the ridges between the conduits.

Yet another variation may have a contact film with one or more columnar through-holes which extend from the surface of the contact film. A second film having one or more through-holes corresponding to respective through-holes may be placed atop and sealed to the contact film with the respective holes aligned. The channels formed by the columns of through-holes allow for wicking of wound exudate to the hydrophilic absorbent material, while the spaces between the films may accordingly allow for the passage of oxygen therethrough for diffusion through the contact film and into the underlying wound.

Yet another variation would be the substitution of extruded small silicone tubes or multilumen silicone extrusions for the coated multifilament fibers.

Another variation may include the substitution of a planar array of hydrophobic multifilament fibers embedded in and completely encapsulated by a thin slab of, e.g., silicone, for the coated multifilament fibers where channels for exudate flow from the wound to the hydrophilic absorbent material may have interruptions in the encapsulating silicone slab. For example, several multifilament hydrophobic fibers may be embedded in each of a number of narrow thin slabs arranged in parallel, the gaps between the narrow thin slabs serving as such channels.

Any of the wound dressing variations may optionally utilize mechanisms for increasing the oxygen availability to the wound while still allowing for exudate to pass into the hydrophilic absorbent material. For example, a flattened silicone bag or a plurality of defined conduits may be formed through the dressing to circulate an oxygen enriched gas mixture, or an oxygen-carrying fluid such as oxygenated water or oxygenated perfluorocarbon solutions through the dressing to increase the oxygenation to the wound and to also prevent the formation of an oxygen gradient. A pump may be optionally integrated either with the dressing or it may be fluidly coupled to the dressing and worn or carried separately by the patient.

Another variation may have a wound dressing with an oxygen reservoir integrated with the dressing. A pump may be optionally coupled fluidly to the reservoir and the reservoir may also be accessible for re-filling or for filling with other agents or fluids, as described herein, or it may alternatively be removed entirely from the dressing and replaced with a substitute reservoir.

Another variation may comprise an oxygen conductive assembly such as an array of coated fibers with gaps or through-holes between to permit fluid to pass through from the wound and a removable, replaceable hydrophilic absorbent material partially enveloped in a hydrophilic absorbent material envelope affixed reversibly thereto, permitting replacement of the hydrophilic absorbent material when it becomes saturated with exudate without the need to detach the oxygen conductive assembly from the patient.

In manufacturing a wound dressing with the features described, various methods may be used for forming the dressing. One variation would be the substitution of extruded small silicone tubes or multilumen silicone extrusions for the coated multifilament fibers. Another variation may involve several rods each having, e.g., a rectangular cross-section, aligned adjacent to one another along a planar surface. With the rods aligned, spacing rails may be secured along one or both ends of the rods to at least temporarily secure the position of the rods relative to one another. A silicone resin film may be swept out upon the rods and the spacing rails may be removed and the rods may be separated individually before the resin film cures and then be positioned upon a cylindrical spool. Because of the rectangular cross-sectional shape of the rods, parallel gaps may be formed between each adjacent rod.

One or more lengths of fibers may be dragged or passed through an oxygen permeable hydrophobic solution, e.g., silicone resin, and then wound onto the spool by rotating the spool such that the coated fibers are wound adjacent along the length of the spool. Once the resin has cured, one or more longitudinal cuts may be made through the spooled coated fibers and the completed coated fiber array may be removed from the spool.

Yet another variation may have a common length of coated fiber wound in an alternating manner with a common length of coated fiber upon a supporting frame. The width of the frame may correspond to the desired width or length of the coated fiber array which contacts the wound region. With the coated fibers wound parallel to one another and secured, one or more adhesive stripes may be laid transversely across the width of the coated fiber array such that formed gaps are defined between the respective stripes. Once the adhesive stripes have cured, the secured coated fiber array may be removed from the supporting frame. The coated fiber array may then have a film applied to the coated fiber array such that an open area formed in the film is positioned over the coated fiber array. The hydrophilic absorbent material may then be laid atop the open area of the film, in contact with the coated fiber array and the film and optionally secured with an adhesive.

With the coated fiber array and hydrophilic absorbent material so arranged, the film may be wrapped to cover and completely envelope the assembly while leaving the coated fiber array exposed within the open area for contacting the wound. The terminal ends of the coated fibers may make contact with an oxygen source, such as ambient air for passive diffusion into an antenna area or other oxygen source as described above. To complete the wound dressing, a border of adhesive may be framed around the coated fiber array and hydrophilic absorbent material so as to leave the open area exposed for contact against the wound. The coated fiber array and hydrophilic absorbent material assembly may be adhered or otherwise secured to the adhesive border, which may be trimmed to form the border. The border may thus allow for the dressing to be secured over a wound such that the exposed coated fibers along the open area directly contact the wound while border prohibits or inhibits any exudate from wicking laterally along the dressing and maintaining a hermetic seal.

BRIEF DESCRIPTION OF THE DRAWINGS

FIGS. 14A to 14C illustrate another variation for manufacturing a composite fiber array in combination with a fluid absorbent material.

DETAILED DESCRIPTION OF THE INVENTION

In covering wounds to facilitate healing, wound dressings are provided which maintain a high availability of oxygen, provide for removal of exudate, prevent toxin accumulation, minimize evaporation, and maintain a moist environment. Furthermore, all wound dressings should prevent contamination, inhibit infection and prevent re-injury of the healing wound. Such a wound dressing may also optionally allow for the administration of various agents or medicines directly to the wound site. Healing may thus be enhanced by providing conditions at the wound site with dressings which are conducive to cell survival and growth in the underlying tissue while preventing cells from dying. Because the wound dressing is sealed to prevent dehydration of the wound, the dressing may be entirely waterproof while preventing adhesion to the wound allowing for normal lifestyle activities including bathing and accelerating healing time.

One variation for a wound dressing which provides for oxygenation of the underlying wound may utilize a hydrophobic fiber mat or other hydrophobic structure interposed between an optional wound-contacting membrane and a sponge or other absorbent material to provide gas-filled conduits for oxygen conduction. The wound dressing may be flexible to enable conformance against the wound anatomy. In the body, cells are typically no more than about 200 microns from the capillaries supplying oxygen and the air conducting conduits in the wound dressing may similarly present an equivalent of an oxygen diffusion barrier of a 200 micron water barrier or less between the wound and the air conducting conduit.

Wound Dressings

Figure 1A:
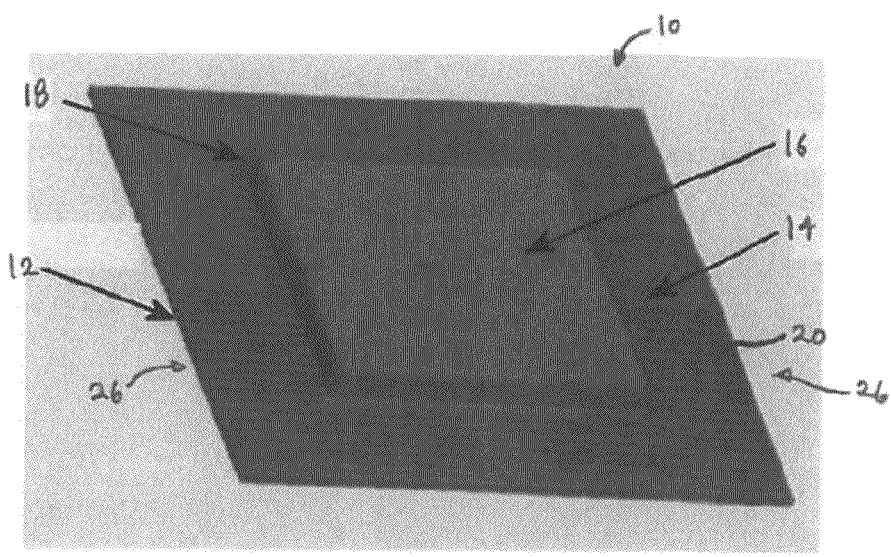
FIGS. 1A to 1C illustrate perspective, side, and bottom views, respectively, of one variation of a wound dressing which comprises a plurality of oxygen conducting fibers or conduits and a hydrophilic absorbent material in communication with an underlying wound.

FIG. 1A shows a perspective view of such a variation in wound dressing 10 which generally comprises a plurality of fibers 12, e.g., multifilament fibers or threads made from materials such as polypropylene or polyethersulfone, which may be coated with an oxygen diffusive hydrophobic material such as a thin silicone coating over the exterior of the fibers 12 such as a low-viscosity acetoxy-cure silicone. In coating the fiber exterior, the fibers may be optionally first permeated with a fluid such as water, ethanol, isopropanol or mixtures thereof (such as 30% to 70% isopropanol) to prevent the hydrophobic solution from wicking into and between the filaments. Once the coating has been placed over the fiber, the fluid may evaporate ensuring that the spaces between the filaments are open for oxygen passage. Alternatively, the fibers 12 may be permeated with fluid and then embedded in silicone. Before the silicone resin cures, the fibers 12 and silicone resin may be embedded between thin cured films or pre-formed and uncured films. In yet another alternative, the external surfaces of the coated fibers 12 may be treated to improve wettability.

In yet other variations, the hydrophobic coated fibers 12 may be microperforated to facilitate the oxygen diffusion through the coating but which may also exclude any aqueous fluid permeation via surface tension effects. In some other variations, various surface treatments, e.g., plasma treatment, chemical modification, etc., may be applied to the coating over the fibers to make the external surfaces of the oxygen conduits hydrophilic to facilitate exudate removal from the underlying wound.

The fibers 12 may also range in size and construction, e.g., about 40 to 2000 micron diameter threads or more particularly about 80 to 260 micron diameter threads with anywhere from 2 to several thousand filaments or more particularly 6 to 8 filaments per fiber. These fibers may be entwinded, twisted, woven, or lie parallel. These coated fibers 12 may be aligned adjacent and parallel to one another along the wound surface 10 and a hydrophilic absorbent material 16 may be positioned over at least a portion of the coated fibers 12 such that the hydrophilic absorbent material 16 is optionally positioned at a distance from the wound surface when in use. Because the hydrophilic absorbent material 16 is separated from the wound by the coated fibers 12 the hydrophilic absorbent material 16 does not directly contact the wound and hence will not irritate or become engrafted into the wound.

The hydrophilic absorbent material 16 may comprise any number of hydrophilic absorbent materials that freely allow for the absorption of large molecules and particulates. The hydrophilic absorbent material may also inhibit or prevent gel polarization or fouling within the hydrophilic absorbent material. For example, in one variation, the hydrophilic absorbent material 16 may be comprised of an open-cell foam, hygroscopic sheets, films, or beads which attract and hold water may also be used as hydrophilic absorbent materials. Examples of hygroscopic materials which may be used may include, for instance, dextranomer, polyacrylamide, etc. Use of such hygroscopic materials may prevent any exudate from being inadvertently squeezed back into the wound site by external massaging and they may also provide a force for pulling or drawing exudate from the wound.

Figure 1B:
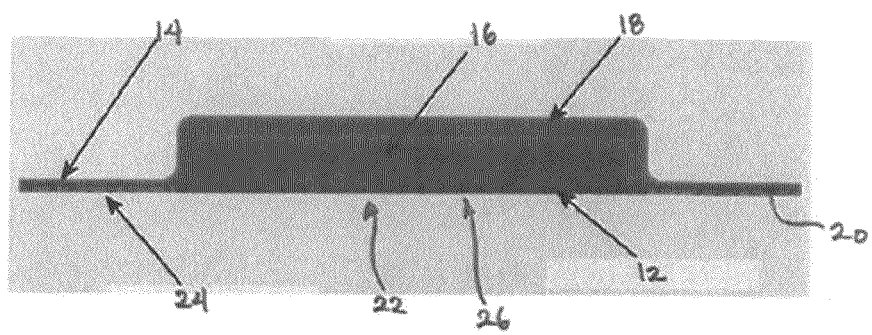

The hydrophilic absorbent material 16 may be coated or otherwise covered by a hydrophilic absorbent material envelope 18 (e.g., silicone, PVC, polyester, polyamide, or any other material which exhibits a low water vapor permeability) and which coats or covers the hydrophilic absorbent material 16 above the coated fibers 12, as shown in the side view of FIG. 1B. The hydrophilic absorbent material envelope 18 may be hermetically sealed to help maintain a sterile environment at the wound site. Any fluids or exudate from the wound may wick between the gaps formed by the adjacent coated fibers 12 and into the hydrophilic absorbent material 16 while the hydrophilic absorbent material envelope 18 may prevent or inhibit evaporation from the hydrophilic absorbent material 16 so that solutes in the exudate do not become concentrated through evaporation of water from the exudate in the hydrophilic absorbent material 16.

While the hydrophilic absorbent material envelope 18 may help to prevent excessive evaporation, the hydrophilic absorbent material envelope 18 may be optionally removed or breached to encourage evaporation, if so desired. One or more openings or ports in the hydrophilic absorbent material envelope 18 may allow the addition of fluids or liquids (optionally with drugs or other agents) or removal of accumulated wound exudate.

The hydrophilic absorbent material 16, if wet, may lessen wound dehydration and allow drug administration while the conduits may continue to provide rapid oxygen diffusion to the wound. Alternatively, the hydrophilic absorbent material 16 may be pre-moistened with any number of agents (e.g., colloidal silver or other antimicrobial solutions, coagulants, anticoagulants, epinephrine, wound-healing promoters, inflammation inhibitors, wetting agents, etc.) either in the original package or added directly to the hydrophilic absorbent material 16 prior to or after application of the dressing to the wound. Prior to application of the dressing 10 to the wound, the wound site may be debrided (if necessary or desired) and an antimicrobial agent such as, e.g., colloidal silver, or a cell containing preparation e.g. platelet rich plasma, stem cells, or skin grafts may be applied directly to the wound. The dressing 10 may then be placed upon the wound. The dressing 10 may also be applied to wounds to enhance the benefits of, e.g., platelet gel, plasma concentrate, white cells, stem cells, skin grafts, etc.

Figure 1C:
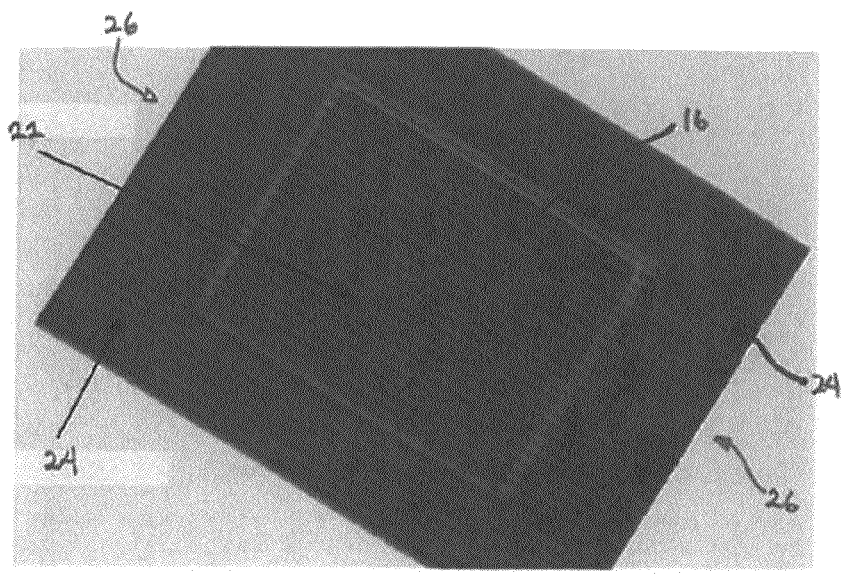

With the hydrophilic absorbent material 16 situated, the coated fibers 12 may extend beyond the hydrophilic absorbent material 16 longitudinally and/or laterally to form a border 20 surrounding the hydrophilic absorbent material 16, as shown. The portion of the coated fibers 12 forming the border 20 may be coated or the gaps between adjacent coated fibers 12 may be otherwise filled with oxygen permeable materials, e.g., silicone, and the underside of the border 20 may have an adhesive 24 formed thereupon such that when the dressing 10 is placed over the wound, an open area 22 exposing the coated fibers 12, as shown in the perspective view of FIG. 1C, may be placed into direct contact against the wound. With the coated fibers 12 placed against the wound, the barrier between the wound and the coated fibers 12 may range anywhere from, e.g., 50 to 300 micron or less, to facilitate the diffusion of oxygen from the coated fibers 12 to the underlying wound. The adhesive 24 along border 20 may encircle the wound such that any exudate from the wound is prevented or inhibited from wicking laterally by the border 20. Instead, the exudate may wick between and through the gaps defined between the coated fibers 12 along the open area 22 and directly into the hydrophilic absorbent material 16 where it may be retained by the hydrophilic absorbent material envelope 18. In other variations, rather than using an adhesive 24 along border 20 (or in addition to), the dressing 10 may be secured to the wound with a separate bandage, e.g., an elastic bandage such as an ACE bandage, which may be wrapped about the patient rather than adhered directly to the surrounding skin.

With the coated fibers 12 extending through the dressing 10, at least one of the terminal ends of the coated fibers 12 may be left with open terminal ends 26 along either or both ends of the dressing 10 extending through the border 20. The open terminal ends 26 of the coated fibers 12 may provide openings for the additional entry of ambient air or other oxygen source for passage through the length of the coated fibers 12. Thus, while the coated fibers 12 form oxygen conduits 14 where oxygen in the ambient air or other oxygen source may pass or conduct through the coated fibers 12 (from the fiber terminal ends 26 as well as through diffusion through the coating) and further diffuse directly through the coating and into the wound site, exudate may be prevented from entering into and fouling the coated fibers 12 by their coating as the exudate passes into the hydrophilic absorbent material 16. The external surfaces of the coating may be rendered hydrophilic to facilitate wicking of exudate from the wound site to the hydrophilic absorbent material.

In alternative variations, rather than having the coated fibers 12 forming the airway passages, oxygen conduits or channels 14 may be formed as hollow channels or passages with no multifilament fibers or threads for allowing the passage of the air or other fluids through. Such hollow oxygen conduits or channels 14 may be used within any of the embodiments described herein in place of the coated fibers 12.

The coated fibers 12 (particularly along the open area 22 where the fibers 12 are coated but not supported by additional silicone filler) may be bonded to one another by silicone stripes which are formed transversely to the coated fibers 12 and which also provide for a smooth wound contacting surface and also prevent fluid accumulation between the coated fibers, as described below in further detail. These transversely coated areas may be sufficiently wide while still allowing for sufficient removal of exudate through the intervening spaces to prevent any excessive exudate pooling as the width and spacing of these transversely stripes may affect how far the exudate travels to find a path from the wound surface and to the hydrophilic absorbent material 16.

Figure 1D:
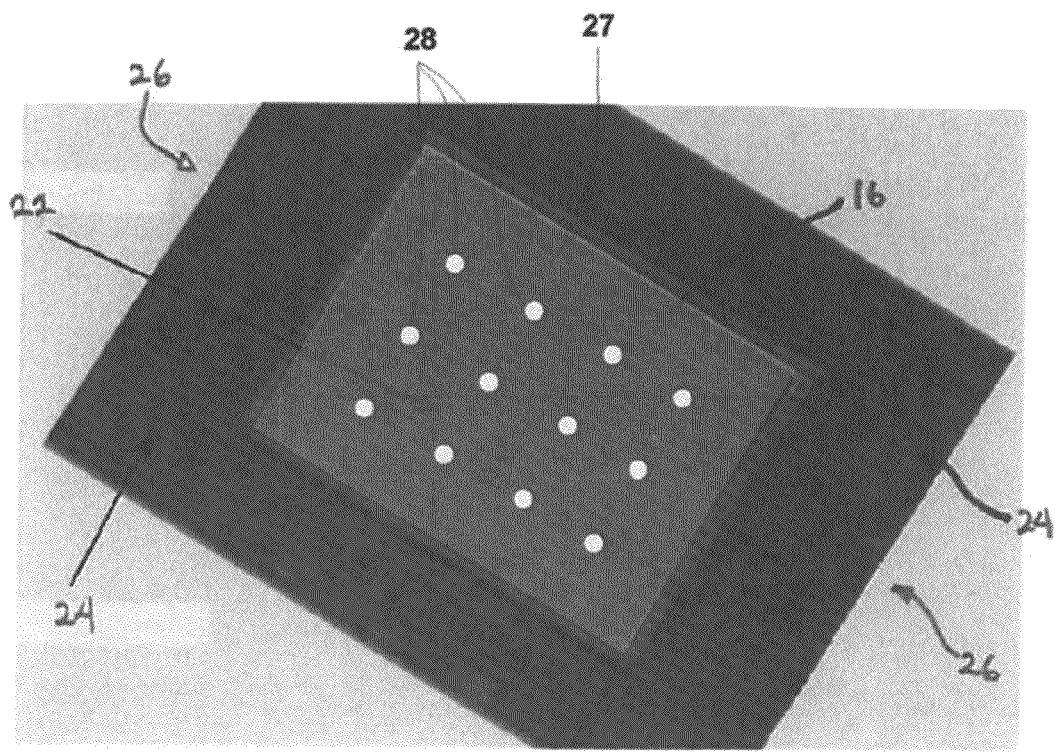
FIG. 1D illustrates a bottom view of another variation of a wound dressing which incorporates an optional membrane for contact against the wound.

While the coated fibers 12 may directly contact the underlying wound, an optional membrane 27 (e.g., perforated silicone) may be interposed over the open area 22 for contacting the wound W instead, as shown in the perspective view of FIG. 1D. In the event that a membrane 27 is used, such a membrane may be relatively thin and may further prevent adhesion to the wound. Other examples of membranes 27 may include thin, highly perforated non-stick materials utilized as the wound contacting surface, such as the Telfa® "Ouchless" non-adherent dressing (Kendall Co., Boston, Mass.). Optional hydrophilic channels 28 may extend from the membrane and through the coated fibers 12 to the overlying hydrophilic absorbent material 16 to allow for the conduction of exudate or infusion of various agents or drugs (e.g., epinephrine, antibiotics, wound healing promoters, coagulants, anticoagulants, anti-inflammatories, analgesics, etc.). The membrane 27 may resist adhering to or integrating with the wound.

In some instances, proteins and other factors in the wound exudate may prove beneficial to wound healing, and therefore removal of bulk wound exudate may be disadvantageous or contraindicated. Rather, the suspending fluid of the wound exudate may be removed while leaving the protein and other macromolecular solutes in situ. The underlying membrane 27 which contacts the wound may be alternatively comprised of an ultrafiltration membrane that prevents macromolecular or cellular constituents of the exudate from escaping the wound site. The membrane 27 may have a structure that allows lateral diffusion so that fluid is readily conducted between the entire wound surface and the hydrophilic channels.

Osmotic pressure developed across the membrane 27 by solutes to which the membrane 27 is impermeable may tend to drive water across the membrane 27. By adjusting the concentration of solutes to which the membrane 27 is impermeable on the side of the membrane facing the hydrophilic absorbent material 16, the flux can be directed in either direction. For example, a high concentration of albumin in the hydrophilic absorbent material 16 would drive water away from the wound while pure saline would drive water toward the wound. If a reverse osmosis (RO) membrane were used, adjusting salt concentration in the hydrophilic absorbent material 16 would have a similar effect. Other forces which can be used to drive the direction of fluid flow include capillary force and hygroscopic polymer swelling. Removal of water from the wound may offer the additional advantage of concentrating healing and growth-promoting factors at the wound site.

Figure 1E:
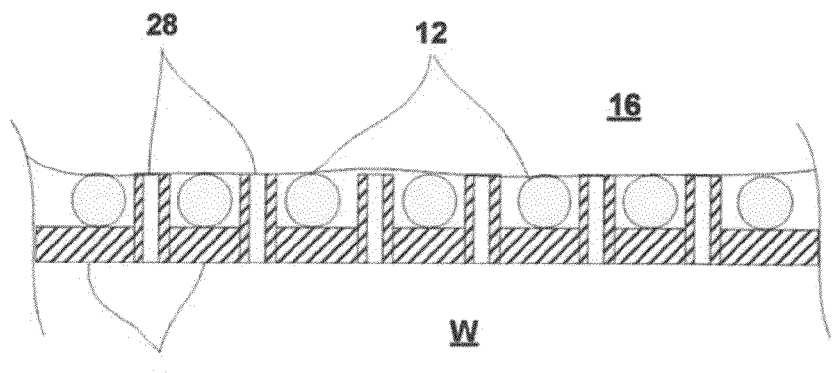
FIG. 1E illustrates a detail partial cross-sectional side view a variation of a contacting membrane having a plurality of exudate channels interspersed between the oxygen conductive conduits.

Optionally, an array of vertically oriented conduits (e.g., open, hollow air-filled tubes such as conduits 28) may extend through hydrophilic absorbent material 16 to bring oxygen from above to the underlying wound-contacting membrane 27 surface, as shown in the detail cross-sectional side view of FIG. 1E. To maximize uniformity of oxygen supply to the tissue, the conduits may be small and closely spaced. The conduit termini may be sealed to liquids by a thin oxygen permeable film to prevent flooding of the conduit by exudate, water or other liquids (e.g. medicants) from the external environment.

The hydrophilic absorbent material 16 and dressing 10 may be varied in size depending upon the size of the wound to be treated. Alternatively, the dressing 10 may be formed into any number of standard uniform sizes. Moreover, while the variation shown in FIG. 1A illustrates a rectangular-shaped dressing 10, the dressing may be formed into alternative configurations as well, e.g., circular, square, etc. In the instance where the oxygen conducting conduits are oriented vertically the dressing can be cut to conform to the wound anatomy.

Figure 2A:
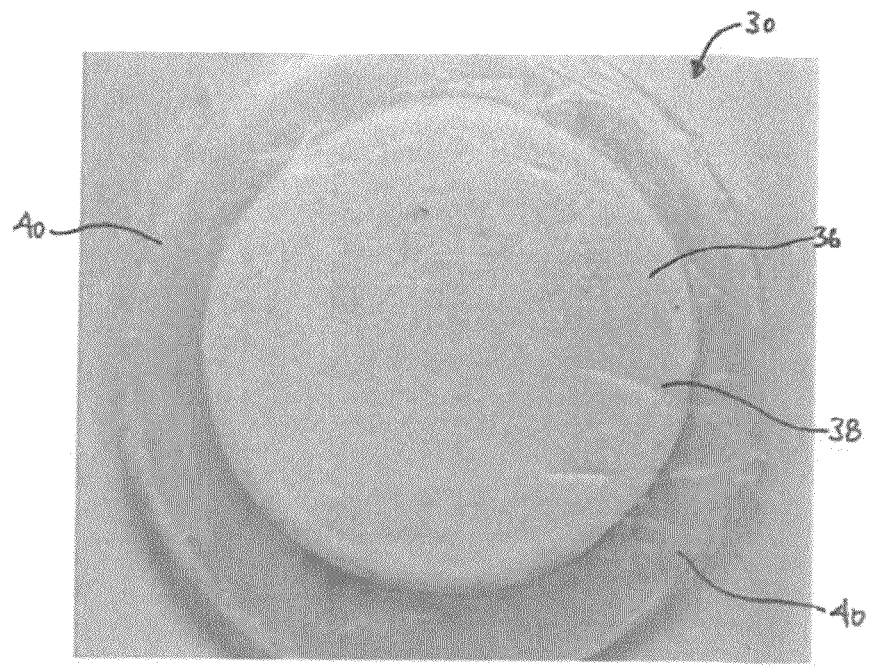
FIGS. 2A and 2B illustrate top and bottom views of another variation of a wound dressing having a circular configuration.
Figure 2B:
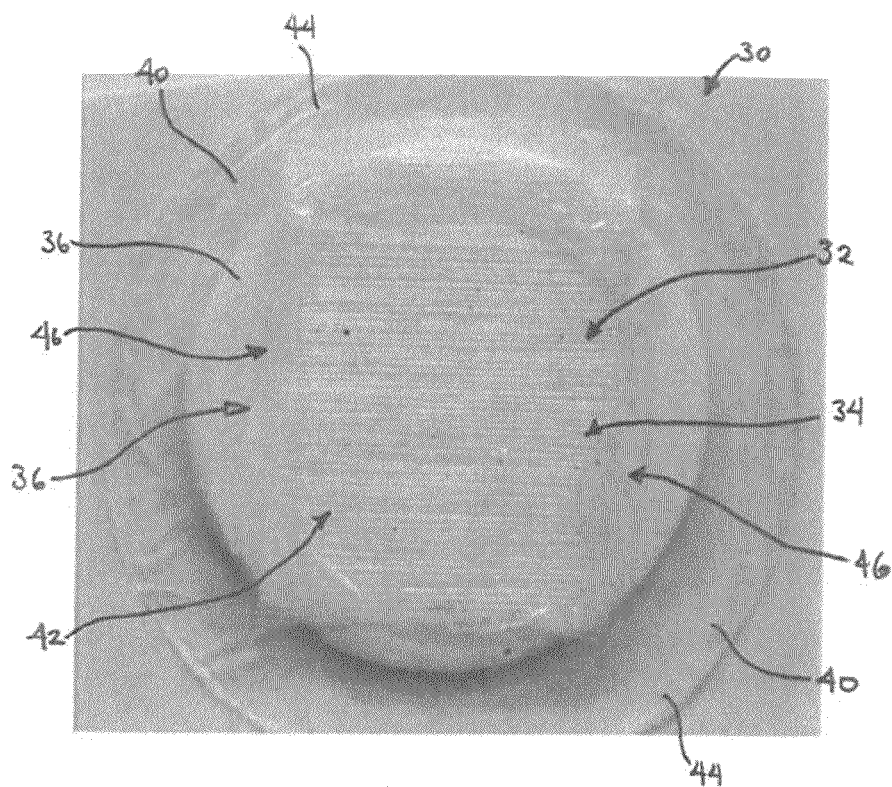

Another variation of wound dressing 30 is illustrated in the respective top and bottom views of FIGS. 2A and 2B which show a circularly-shaped dressing 30. In this variation, the dressing diameter may be, e.g., 3 inches, while the hydrophilic absorbent material 36 may have a diameter of, e.g., 2 inches. The hydrophilic absorbent material 36 may be covered or encased by hydrophilic absorbent material envelope 38 which may also form a border 40 around the hydrophilic absorbent material for contact against the patient's skin. As above, border 40 may be secured to the skin surface surrounding the wound via adhesive 44 and prevent any exudate from wicking laterally of the open area 42 (e.g., having a size of 1.5 in by 1.25 in.) which exposes the coated fibers 32 for contact against the wound. The open terminal ends 46 of the coated fibers 32 may allow for the surrounding air or other oxygen source to enter into and through the coated fibers 32 such that the coated fibers function as oxygen conduits 34 to provide oxygen from the air or other oxygen source directly into proximity to the wound. As described above, the oxygen may diffuse directly from passages in the coated fibers 32 and pass through the surrounding film and into the wound. Alternatively, as previously described, the oxygen conduits or channels 34 may remain hollow rather than having a fiber within.

The open area 42 may have, e.g., about 50 coated fibers 32, aligned parallel to one another and the adjacent fibers may have thread diameters of about 700 microns which are bonded to one another with, e.g., two or more spaced strips of silicone having a width of about 3.175 mm and aligned transversely relative to the lengths of the coated fibers 32. The number of fibers 32 may, of course, be varied depending upon the diameter of the fibers used as well as the dimensions of the open area 42 and size or configuration of the dressing. Moreover, the hydrophilic absorbent material 36 may have a thickness of about, e.g., 2 mm to 2 cm, with an exudate absorbing capacity of about, e.g., 1.5 cc to 15 cc.

As discussed, although specific dimensions are presented they are intended to be illustrative and the size and configuration of the wound dressings may be varied depending upon the wound to be treated. Moreover, the dimensions such as thread diameters, thicknesses of coating and films or the number of fibers used may be used in any of the different variations or embodiments described herein.

Figure 3A:
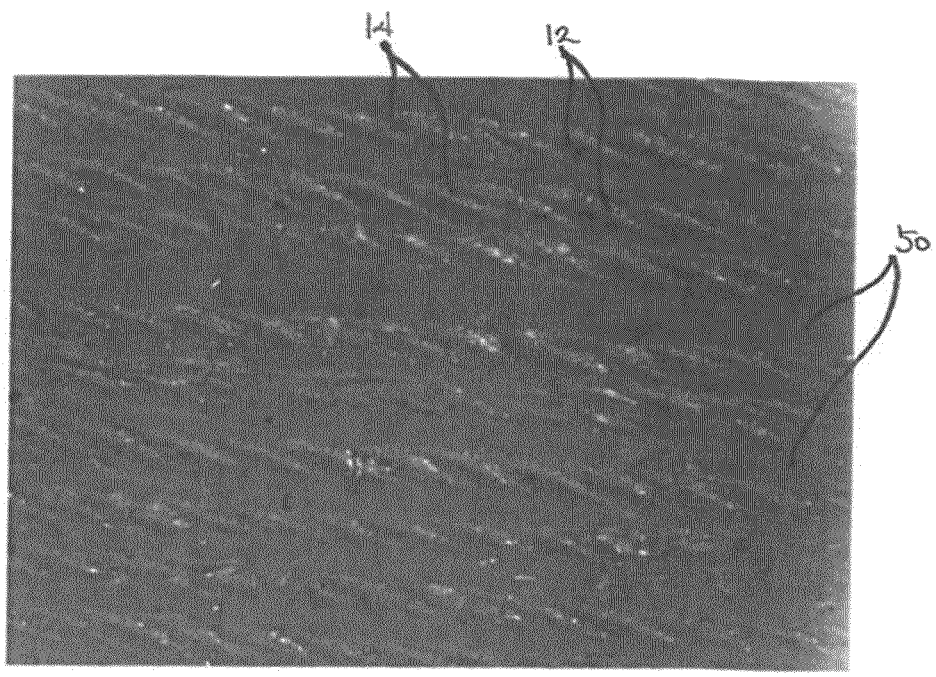
FIG. 3A illustrates a detail bottom view of the oxygen conduits and fibers aligned adjacent to one another.
Figure 3B:
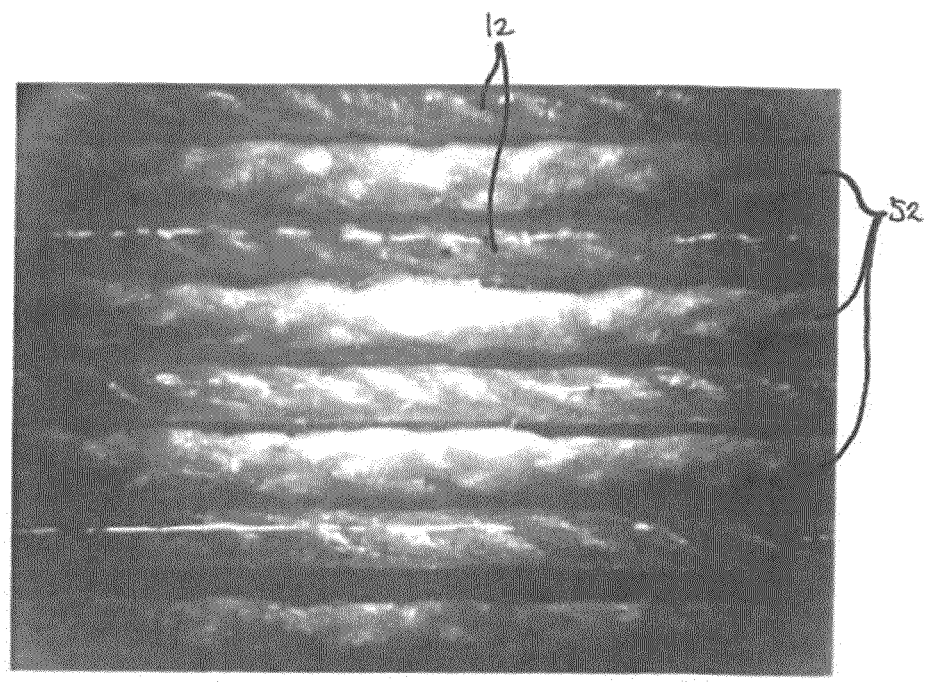
FIG. 3B illustrates a detail bottom view of another variation of coated oxygen conductive fibers aligned with hydrophilic fibers.

FIG. 3A shows a detail bottom view of a dressing illustrating an example of threads or multifilament threads which may be covered or coated to form individual coated fibers 12 which may then be aligned parallel to one another to form the oxygen passageways. Alternatively, oxygen conduits or channels 14 may be formed as hollow passageways, as previously described. The gaps between the individual adjacent coated fibers 12 may be left open to allow for any exudate to wick through to the hydrophilic absorbent material. Alternatively, the gaps may have an interrupted, discontinuous filler 50 material interspersed or formed such that the gaps between the fibers are mostly filled leaving gaps for transit of wound exudate from below and optionally medicants from above. Such fillers 50 may include any of the materials described herein, e.g., silicone, and may be used to contact against the wound along with the fibers. In yet another alternative, FIG. 3B shows another detail bottom view where one or more hydrophilic fibers 52 or wicking fiber (e.g., absorbent fibers such as cotton) may be interspersed between the coated fibers 12 to conduct exudate away from the wound or medicants to the wound surface. Although the variation shows hydrophilic fibers 52 alternated with the coated hydrophobic fibers 12, the number and positioning of the hydrophilic fibers 52 may be varied in various other patterns, e.g., hydrophobic fibers 52 may be interspersed between every two fibers 12 or so on, or they may be omitted completely as well. Moreover, the diameter of the coated fibers 12, e.g., 700 microns, may be similar or identical to the diameter of the hydrophobic fibers 52 although the diameters may also be varied depending upon the desired wicking properties.

Figure 3C:
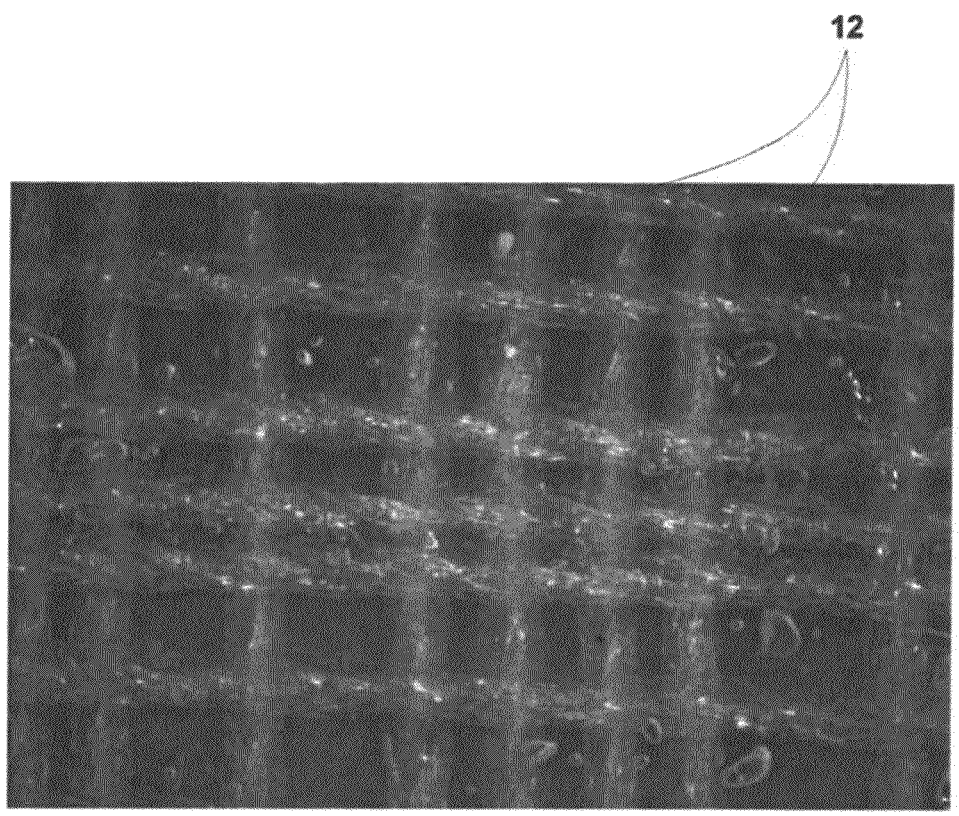
FIG. 3C illustrates a detail bottom view of yet another variation of coated fibers which are transversely aligned relative to one another.

Another alternative is shown in the detail bottom view of FIG. 3C. In this variation, the individual fibers 12 may be positioned in a transverse orientation relative to one another. A first set of fibers 12 oriented parallel to one another may be laid atop a second set of fibers 12 which are also parallel to one another such that the first and second set are transverse to one another. Alternatively, the crossing fibers 12 may be interwoven with respect to one another and in other alternatives the crossing fibers may be orientated at some other angle rather than being orthogonal, e.g., 45 degrees relative to one another. The combined thickness of the crossing fibers may still be less than 1 mm. The coated fibers and hydrophilic fibers may be arranged relative to one another in any fashion, including woven, intertwined or knit.

Figure 4A:
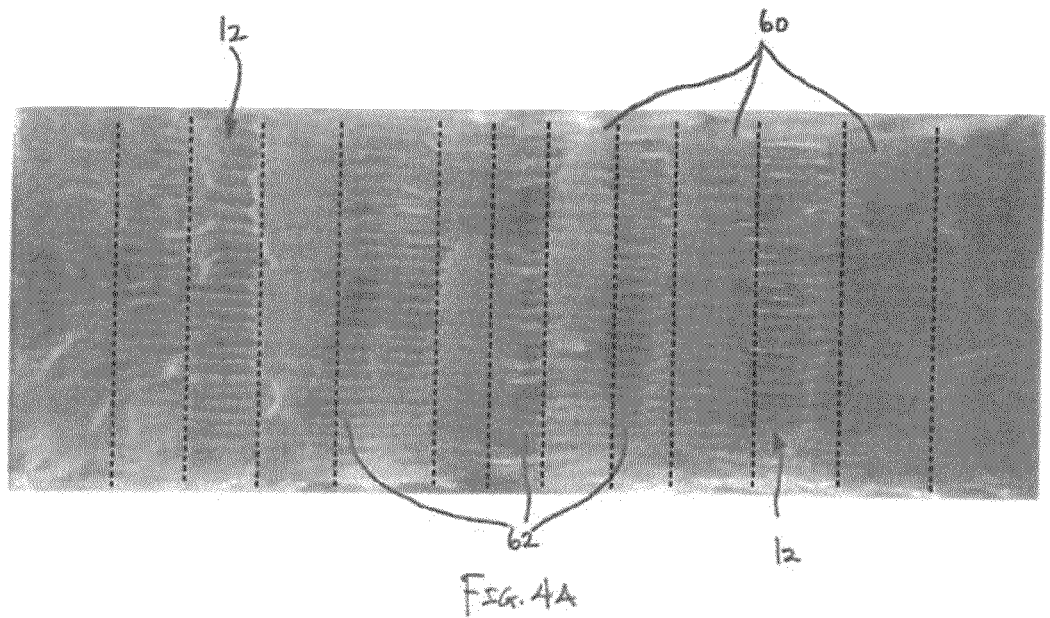
FIGS. 4A and 4B illustrate bottom and top views of another variation where the fiber array may be secured by adhesive stripes transversely aligned relative to the fibers.
Figure 4B:
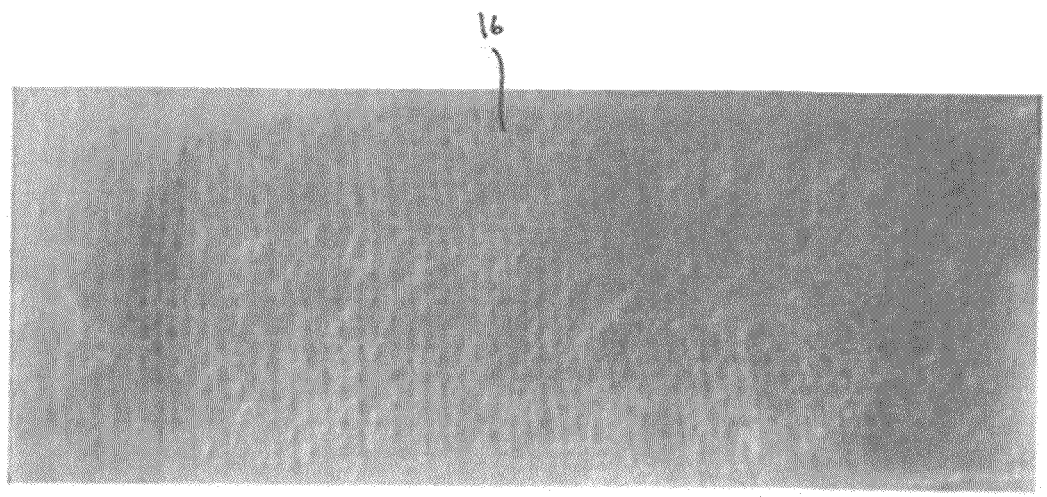

As described above, the coated fibers 12 may be secured to one another via one or more adhesive stripes 60 (e.g., silicone) which are placed across the width of the dressing so as to align perpendicularly relative to the direction of the coated fibers 12. These stripes may take any orientation, including an interrupted flat film that allows passage of fluid from the wound surface to the hydrophilic absorbing material. A detail example is illustrated in the bottom view of FIG. 4A, which shows a plurality of coated fibers 12 which are aligned adjacent to one another and several adhesive stripes 60 placed over and between the fibers. The open gaps 62 left between adhesive stripes 60 may allow for the exudate to pass through and wick into the hydrophilic absorbent material 16, which is positioned atop and in contact with the fibers 12, as shown in the top view of FIG. 4B.

Figure 5A:
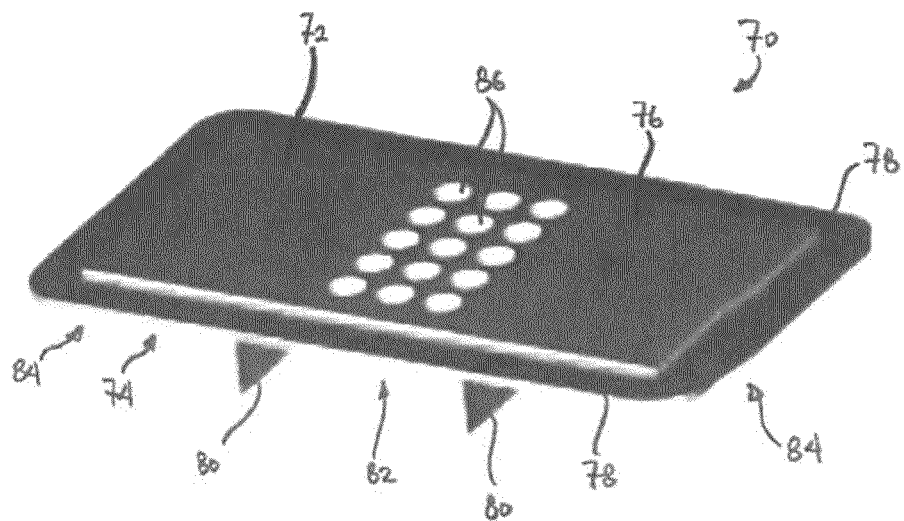
FIGS. 5A and 5B illustrate perspective and partial cross-sectional side views of another variation of a wound dressing having orthogonal channels.

In yet another variation, FIG. 5A illustrates a perspective view of a wound dressing 70 which shows an embodiment having a hydrophilic absorbent material 72 positioned and encased between a contacting bottom layer 74 and a sealing top layer 76 where each of the layers 74, 76 may have a thickness, e.g., of less than 2 mm. An additional layer of silicone film (e.g., 50-100 micron) may be applied over one or both layers 74, 76 to modify the surface and further inhibit any leakage through the layers 74, 76. A bondable skirt 78 may be formed to surround the periphery of the dressing 70. While the wound-contacting bottom layer 74 and sealing top layer 76 may be formed of any of the materials described herein, it may be comprised of a material such as medical grade platinum cure silicone. The layers 74, 76 may be formed with the bondable skirt 78 to provide an area for bonding and sealing the layers to one another around the hydrophilic absorbent material 72.

Figure 5B:
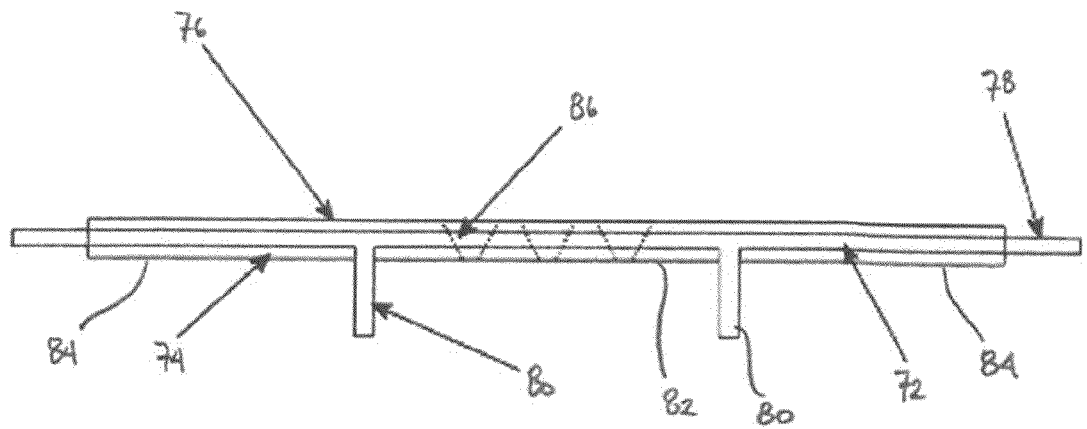

The dressing 70 may also be formed with one or more bondable wings 80 formed into the dressing, as shown in the partial cross-sectional end view of FIG. 5B. The bondable wings 80 may be incorporated during the molding process for forming the layers 74, 76 and may be comprised of a material such as felt or fabric which may be mechanically trapped in the silicone to leave the exposed surfaces silicone-free for bonding. The portion of the dressing 70 which contacts the wound may be defined along a wound-contact area 82 which may define one or more through-holes 86, e.g., conical through-holes, which extend from the wound to wick any exudate through the holes 86 and into the hydrophilic absorbent material 72. Also shown are the oxygen conduit 84 which may be formed into the contacting bottom layer 74 for direct contact with the wound surface for facilitating the delivery of oxygen to the wound.

Figure 6:
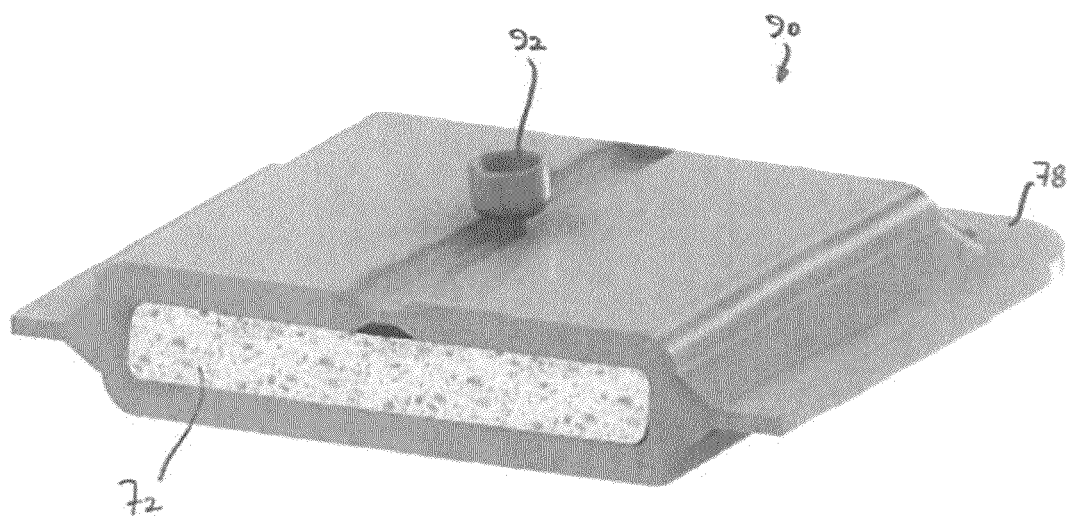
FIG. 6 illustrates a cross-sectional perspective view of yet another variation of a wound dressing having a port.

In yet another variation, FIG. 6 illustrates a perspective view of another wound dressing 90 which is sectioned for illustrative purposes. In this variation, the layers may surround the hydrophilic absorbent material 72 but the dressing 90 may optionally incorporate a port 92 for exudate evacuation or agent introduction, e.g., along sealing top layer 76. Because hydrophilic absorbent material 72 is sealed for preventing dehydration of the wound, port 92 may provide an opening which can be opened or closed to provide access to the interior of hydrophilic absorbent material 72 and dressing 90. For instance, port 92 may be configured as a Luer attachment for facilitating the suction or removal of any excess exudate from the hydrophilic absorbent material 72. Port 92 may also provide an opening through which any number of medicaments or agents may be introduced into the interior of dressing 90 and hydrophilic absorbent material 72 to provide for the infusion of any additional treatments to the wound. Such a port 92 feature may be incorporated into any of the embodiments described herein as practicable.

Additionally and/or alternatively, the hydrophilic absorbent material 72 may be removed from the wound dressing and optionally replaced with a new absorbent material if excess exudate is absorbed into the material 72. The remainder of the wound dressing 90 may be left upon the wound site while the hydrophilic absorbent material is replaced or removed. Alternatively, the wound dressing 90 may be removed from the wound site for replacement of the absorbent material and then replaced upon the wound site. In this variation and others disclosed herein, the absorbent material may be optionally removed and/or replaced in such a manner as described.

Figure 7A:
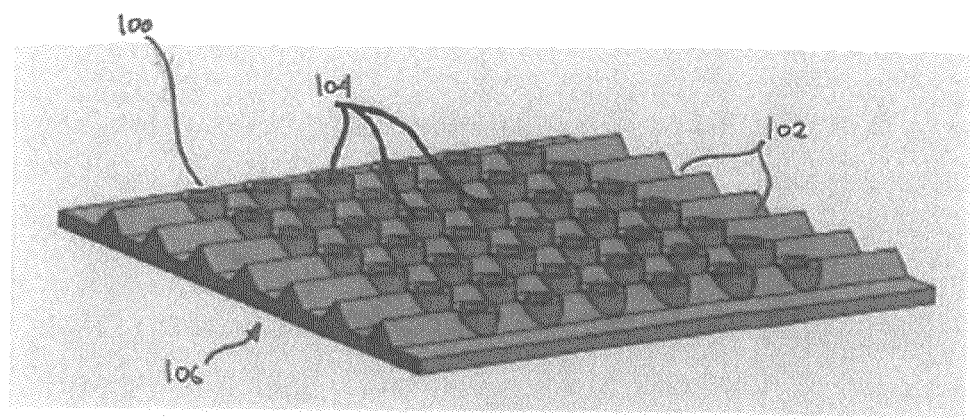
FIGS. 7A and 7B illustrate perspective views of yet another variation of a wound dressing assembly having ridges or undulations which define the oxygen conduits.

Yet another variation is shown in the perspective view of FIG. 7A which illustrates a silicone contact film 100 having one or more ridges or notches 102 formed over its surface on the opposite side of the wound contact surface 106. These ridges or notches 102 may be formed as ridges, undulations, tapered protrusions, or any other projections which extend from the surface to form lateral conduits for oxygen diffusion through the wound contact surface 106. One or more through-holes 104 may be defined to extend in a direction normal to the surface 106 for allowing any exudate to flow from the wound and to the sponge positioned above the contact film 100.

Figure 7B:
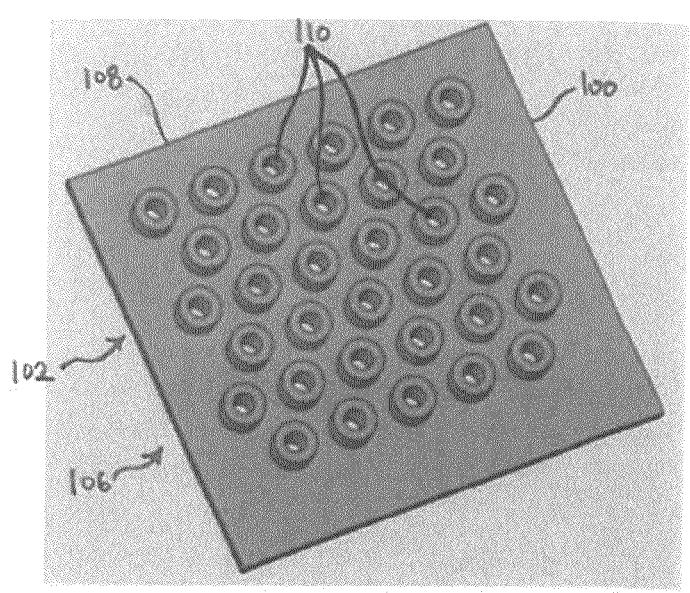

FIG. 7B illustrates a perspective view of a second film 108 which may be laid atop contact film 100 where the second film 108 may define one or more through-holes 110 which correspond to through-holes 104. With the second film 108 positioned atop contact film 106, the open channels formed by the ridges or notches 102 between the upper and lower films may function as the oxygen conduits where the oxygen may then diffuse through the contact film 100 and into the underlying wound.

Figure 7C:
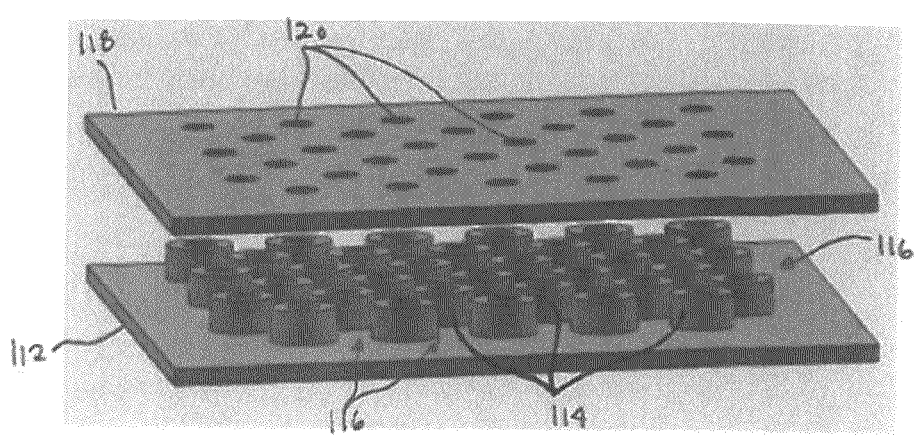
FIG. 7C illustrates a perspective assembly view of another variation where protruding orthogonal channels define the oxygen conduction passages.

FIG. 7C shows a perspective assembly view of yet another variation where contact film 112 may incorporate one or more columnar through-holes 114 which extend from the surface of the contact film 112. A second film 118 having one or more through-holes 120 corresponding to through-holes 114 may be placed atop and sealed to the contact film 112 with the respective holes aligned. The resulting channels 116 formed by the columns of through-holes 114 and between the films 112, 118 may accordingly allow for the passage of oxygen therethrough for diffusion through the contact film 112 and into the underlying tissue. The aligned through-holes 114, 120 may also allow for the passage of the exudate from the wound to the sponge which may be positioned atop the second film 118. The through-holes 114, 120 may also allow for the infusion of various medicaments or agents into the wound.

Figure 8:
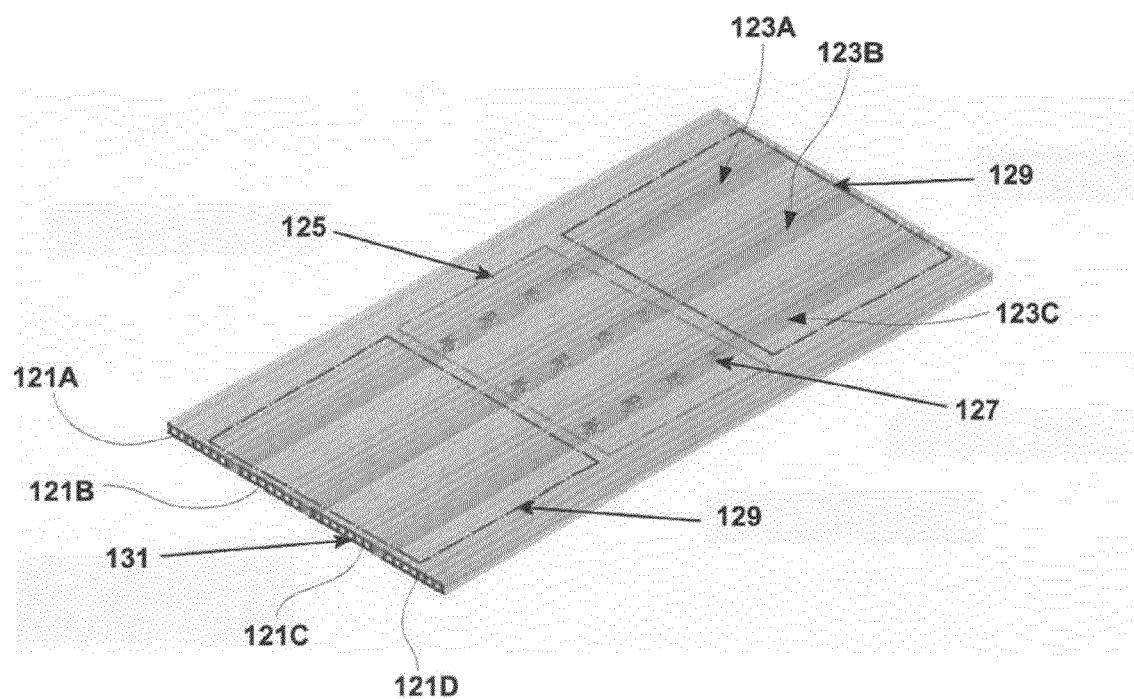
FIG. 8 illustrates a perspective view of a composite fiber array which may be used alone or in combination with other dressings.

FIG. 8 shows a perspective view of yet another variation where a fiber array assembly may be formed by one or more fiber array sub-assemblies 121A, 121B, 121C, 121D. The sub-assemblies may be formed by utilizing any of the methods described herein for creating the oxygen conduits or channels where several conduits may be formed into an individual ribbon. Each of the ribbons forming the sub-assemblies 121A, 121B, 121C, 121D may then be aligned adjacent and adhered or other attached relative to one another. The variation shown illustrates four fiber array sub-assemblies although fewer than four or more than four sub-assembly ribbons may be formed and attached to one another. Moreover, the lengths and widths of each of the sub-assemblies may be adjusted according the size of the wound to be treated or they may be standardized in any number of suitable dimensions.

With the individual sub-assemblies 121A, 121B, 121C, 121D formed and aligned, they may be attached to one another via attachment 123A, 123B, 123C which may comprise any number of suitable attachment methods. For instance, silicone may be applied for maintaining the relative positioning of each sub-assembly along the entire length of the assembly or each individual sub-assembly may be adhered to another layer such as a silicone layer or directly to a hydrophilic fluid absorbent material such as gauze, sponge, or any of the materials described herein.

Regardless of the attachment mechanism, each of the sub-assemblies 121A, 121B, 121C, 121D may be formed with a gap, space, or channel formed between adjacent sub-assemblies to provide a channel or pathway for exudate to pass between the sub-assemblies and the hydrophilic fluid absorbent material which may optionally be placed adjacent to the fiber array. Alternatively, any number of hydrophilic wicking materials or channels 127 may be formed along the gap or channel between the sub-assemblies 121A, 121B, 121C, 121D to facilitate the wicking away of exudate from the underlying wound.

Additionally and/or alternatively, portions of the fiber array may be applied with an adhesive, e.g., adhesive silicone film, for securement to the patient over the wound surface.

As shown, the wound contact region 125 may be formed by the composite fiber array such that the wicking materials or channels 127, if present, may be situated directly over the wound surface. The portions of the fiber array adjacent to one or both sides of the wound contact region 125 may form the oxygen absorption region (antenna region) 129 where oxygen may diffuse into the channels for further diffusion into the underlying wound over the wound contact region 125, as described herein. The ends 131 of the oxygen absorption region 129 may be optionally sealed to prevent exudate from entering into the channels.

As previously described, any of the features of this variation may be combined with the features of other variations. For instance, dressing incorporating the ridges or notches 102 may be used with the port 92 as previously described, if so desired.

Actuated Wound Dressings

Figure 9:
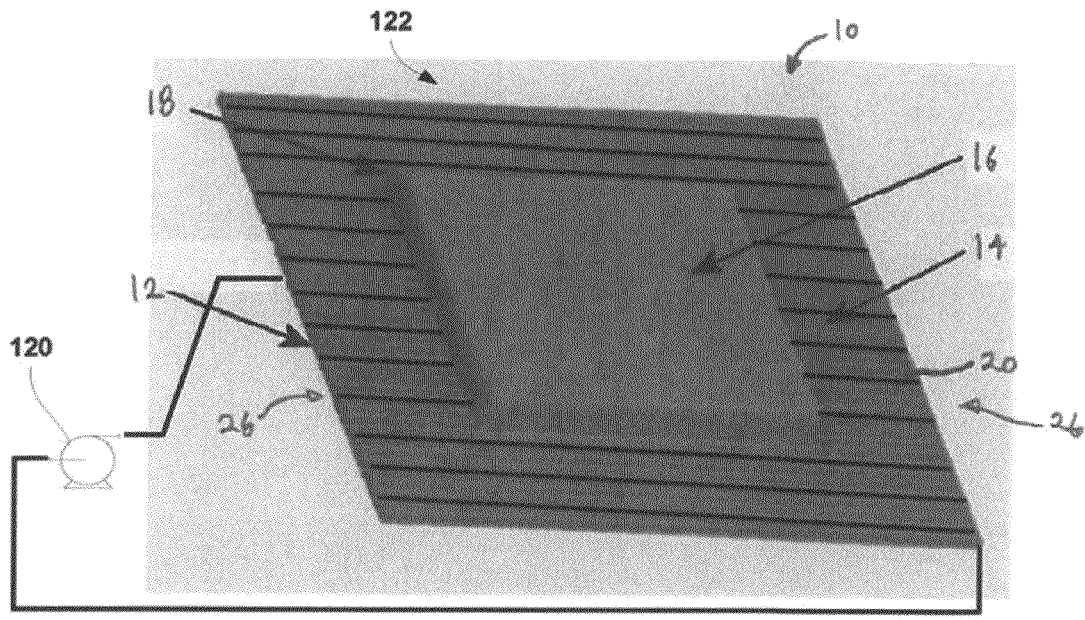
FIG. 9 illustrates a perspective view of yet another variation of a wound dressing incorporating a pumping mechanism.

In yet another variation, any of the wound dressing variations may optionally utilize mechanisms for increasing the oxygen availability to the wound while still allowing for exudate to pass into the hydrophilic absorbent material. FIG. 9 shows an illustrative variation of a dressing having an either a flattened silicone bag or a plurality of defined conduits 122 formed through the dressing. Either the bag or conduits 122 may circulate fluid such as oxygenated water, perfluorocarbons, or gaseous mixtures through the dressing to increase the oxygenation to the wound and to also prevent the formation of an oxygen gradient. Circulating the fluid may allow for the oxygen to diffuse into the conduits 122 and through the silicone membrane into the underlying wound. A pump 120 may be optionally integrated either with the dressing or it may be fluidly coupled to the dressing and worn or carried separately by the patient. Alternatively, rather than circulating the oxygenated fluid, pump 120 may be used to simply pulse the air and/or oxygen or mixtures thereof through the conduits 122.

Figure 10:
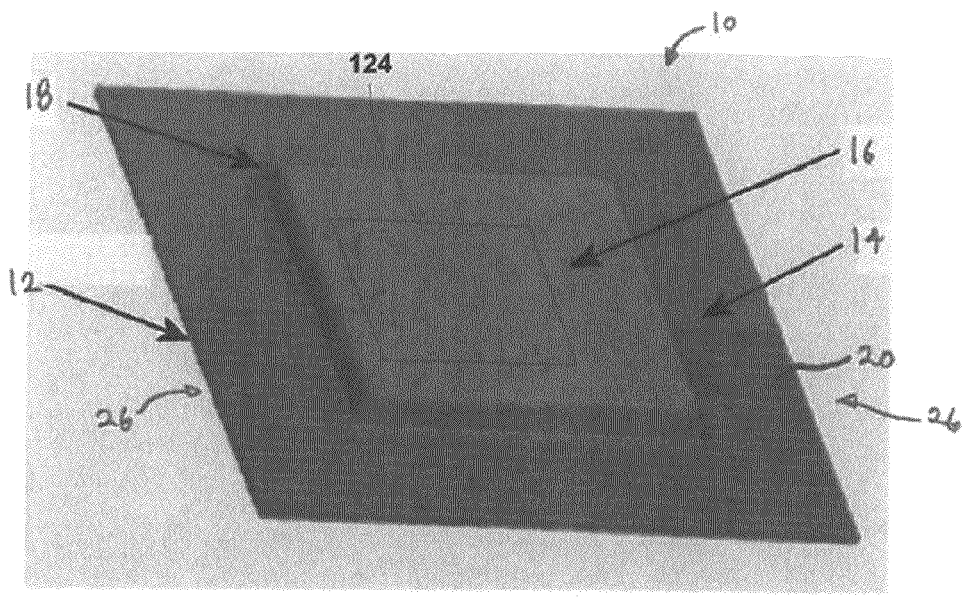
FIG. 10 illustrates a perspective view of yet another variation of a wound dressing incorporating a reservoir.

Another variation is shown in the perspective view of FIG. 10 which illustrates a dressing having an oxygen reservoir 124 integrated with the dressing. Reservoir 124 may contain oxygen for diffusion into and through the hydrophilic absorbent material 16 and for passage either directly into the wound or via the coated fibers 12 and subsequently into the wound. Pump 120 may optionally be a fluid connection to the reservoir 124 and the reservoir 124 may also be accessible for re-filling or for filling with other agents or fluids, where any of the agents or fluids as described herein may be used, or it may alternatively be removed entirely from the dressing and replaced with a substitute reservoir.

Methods of Manufacturing

Figure 11A:
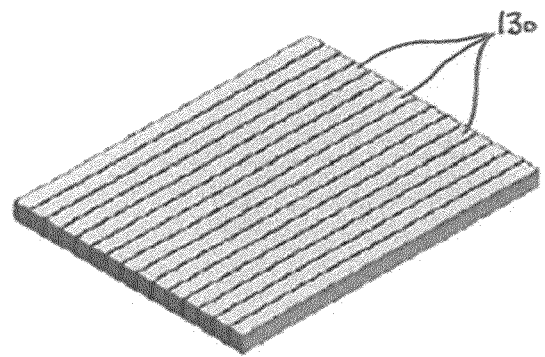
FIGS. 11A to 11F illustrate one variation for manufacturing a wound dressing fiber assembly.
Figure 11B:
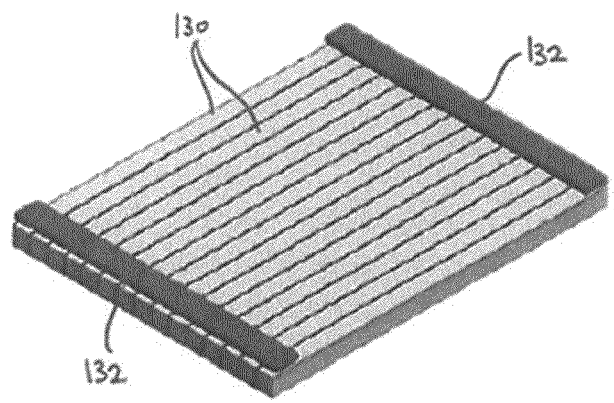
Figure 11C:
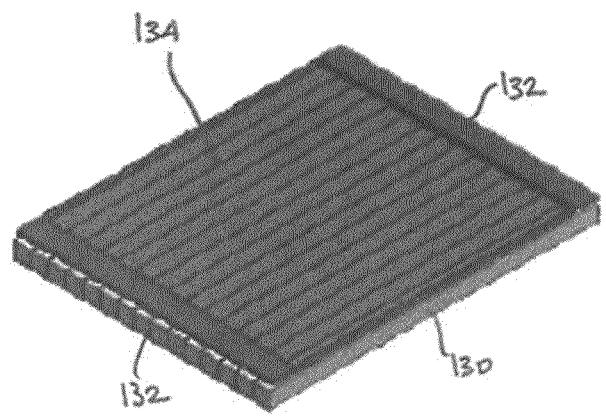

In manufacturing a wound dressing with the features described, various methods may be used for forming the dressing. One variation is illustrated in FIGS. 11A to 11F where hollow or coated fiber oxygen conduits are formed directly onto substrate rods, the latter coated with a bonding polymer e.g. silicone. The several substrates or rods 130 each having, e.g., a rectangular cross-section, may be aligned adjacent to one another along a planar surface, as shown in the perspective view of FIG. 11A. The length and width of the substrates or rods 130 may be varied depending upon the desired size and configuration of the final wound dressing, but one example may utilize the rods having a surface width of, e.g., 0.5 to 1.0 cm. With the substrates or rods 130 aligned, spacing rails 132 may be secured along one or both ends of the rods 130 to at least temporarily secure the position of the substrates or rods 130 relative to one another, as shown in FIG. 11B, as well as to provide a guide for a silicone resin film 134 to be laid atop the substrates or rods 130 and between spacing rails 132, as shown in FIG. 11C. Thus, the spacing rails 132 may have a height which corresponds to the height of the resin film 134 to be laid atop the substrates or rods 130 such that the resin film 134 may be swept out with a straight edge using the rails 132 as a guide. For example, the spacing rails 132 may have a thickness of about 115 microns.

Figure 11D:
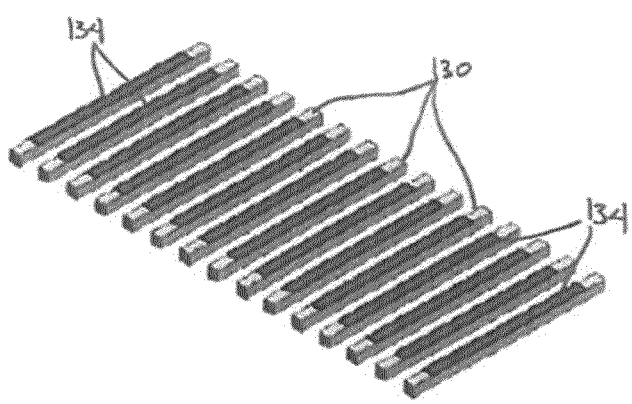
Figure 11E:
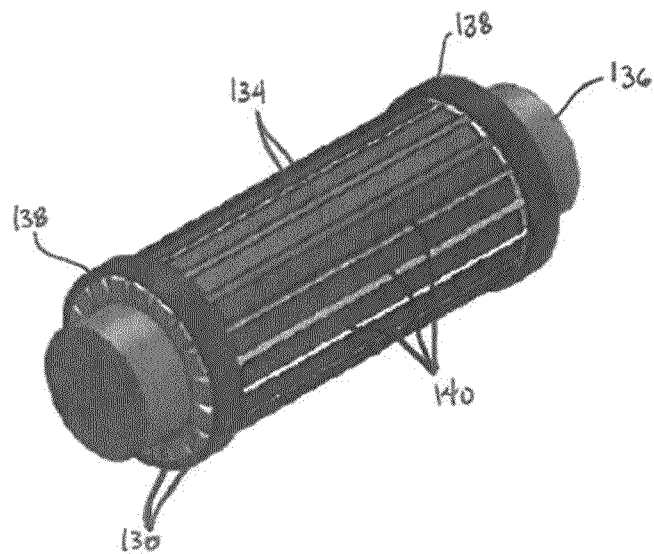

With the silicone resin film 134 swept out upon the substrates or rods 130, the spacing rails 132 may be removed and the substrates or rods 130 may be separated individually before the resin film 134 cures, as shown in FIG. 11D. The substrates or rods 130 may then be positioned upon a cylindrical spool 136 (e.g., having a 1 to 2 in. diameter) and attached via securing members 138, e.g., rubber bands, such that the surface of the substrates or rods 130 opposite to the resin film 134 are placed against the spool surface and the resin film 134 is positioned to face outwardly relative to the spool 136. Because of the rectangular cross-sectional shape of the substrates or rods 130, parallel gaps 140 (e.g., about 1 to 2 mm) may be formed between each adjacent rod 130, as shown in FIG. 11E.

Figure 11F:
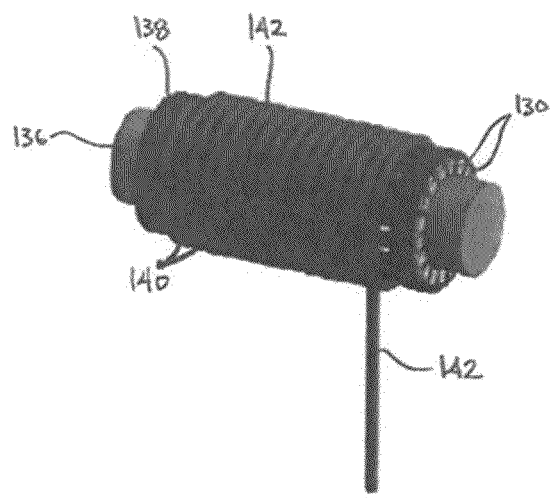

One or more lengths of fibers 142 may then be dragged or passed through a coating solution, e.g., silicone resin, and then wound onto the spool 136 by rotating the spool 136 either automatically or manually such that the coated fibers 142 are wound adjacent along the length of the spool 136, as shown in FIG. 11F. The rotational speed of the spool 136 may be varied, e.g., at 0.1 to 1.0 RPM to yield a pull-rate of about 0.6 in/min. Because the rods 130 with the silicone resin film 134 are spaced apart from one another with gaps 140, the substrates or fibers 142 may be secured to one another with the corresponding gaps 140 formed transversely to the lengths of the fibers 142. Once the film 134 has cured, one or more longitudinal cuts may optionally be made through the spooled fibers 142 and the completed fiber array may be removed from the spool 136.

In dragging or passing the fibers through the hydrophobic solution, the fibers may be first wetted with a fluid such as water or alcohol such as ethanol, isopropanol or mixtures thereof (such as 30% to 70% isopropanol) to prevent the hydrophobic solution from wicking into and between the filaments, as described above. Once the coating has been placed over the fiber, the fluid may evaporate ensuring that the conduits between the filaments are open for oxygen passage. The coating or covering of these fibers as well as the pre-wetting with fluid may be utilized with any of the variations described herein.

Although the spool 136 variation is illustrated with a single common length of fiber 142, other variations may incorporate hydrophilic fibers or other wicking fibers interspersed between the coated hydrophobic fibers 142, as discussed above, or hollow tubes of oxygen permeable material rather than coated threads.

Figure 12A:
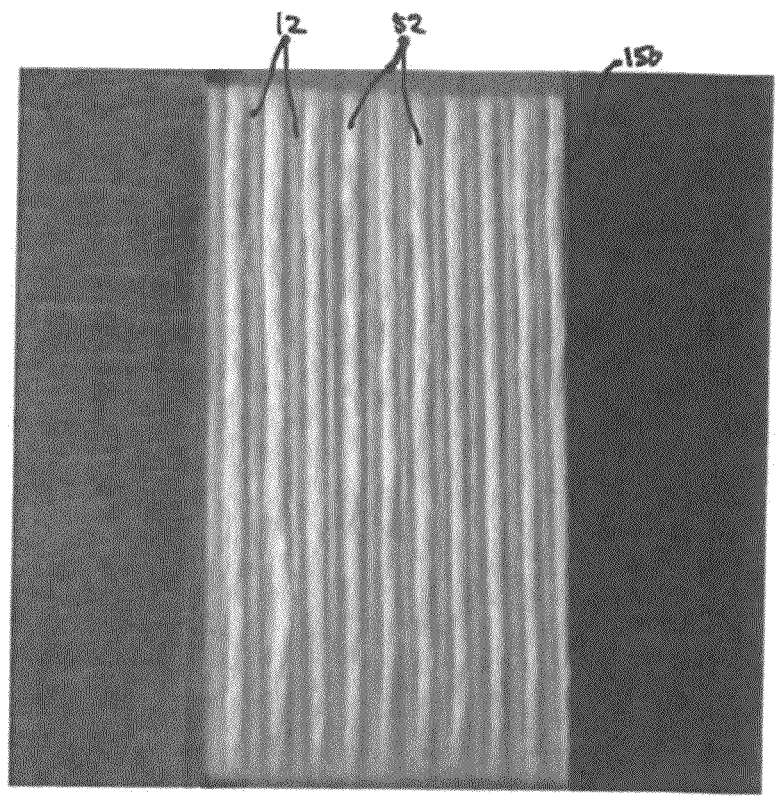
FIGS. 12A to 12P illustrate another variation for manufacturing a wound dressing.

Yet another variation is shown in the top view of FIG. 12A which illustrates a manufacturing method where a common length of fiber 12 may be wound in an alternating manner with a common length of hydrophobic fiber 52 upon a supporting frame 150, e.g., a planar support. The width of the frame 150 may correspond to the desired width of length of the fiber array which contacts the wound region.

Figure 12B:
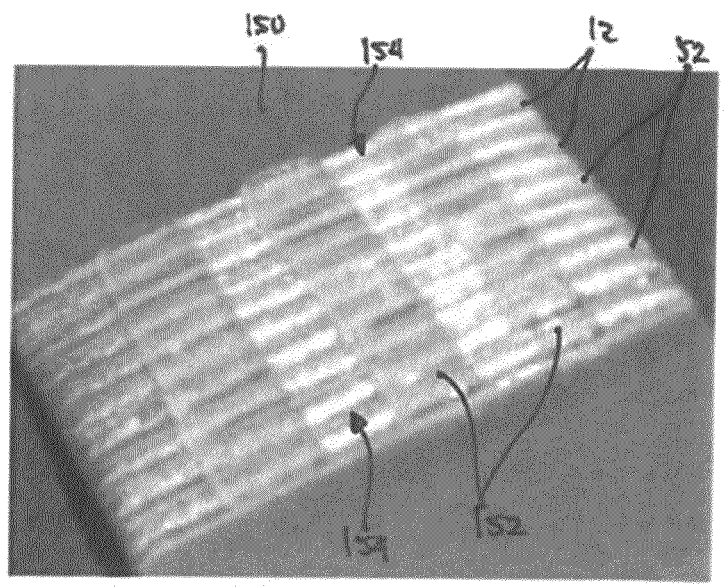
Figure 12C:
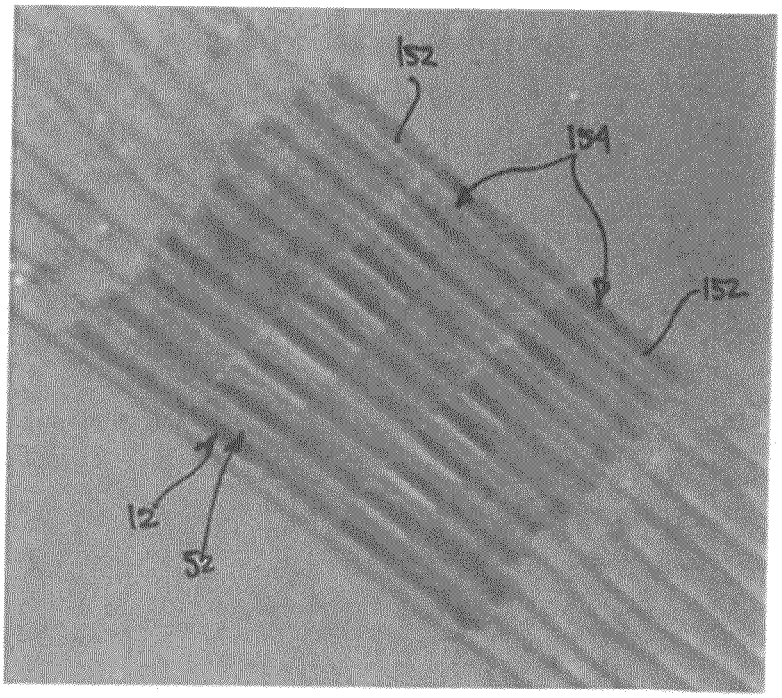
Figure 12D:
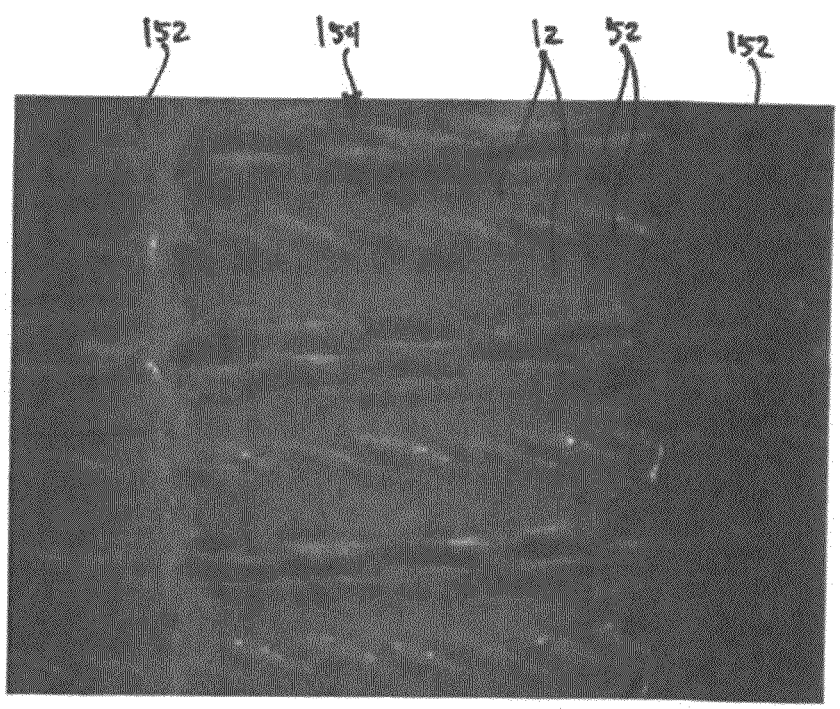

With the fibers wound parallel to one another and secured, one or more adhesive stripes 152, e.g., silicone resin, may be laid transversely across the width of the fiber array such that formed gaps 154 are defined between the respective stripes 152, as shown in the perspective view of FIG. 12B. Once the adhesive stripes 152 have cured, the secured fiber array may be removed from the supporting frame 150, as shown in the perspective view of FIG. 12C. FIG. 12D illustrates a detail bottom view showing how the hydrophobic coated fibers 12 are aligned in parallel in an alternating manner with hydrophilic fibers 52. The adhesive stripes 152 may be seen with the formed gap 154 between exposing the respective fibers 12, 52 for contact against the wound. Alternatively, these materials can be woven, knit, or otherwise entwined in any fashion, providing the oxygen conduction from outside the wound surface is unimpeded and fluid connection between the wound surface and the hydrophilic absorbent material is preserved.

Figure 12E:
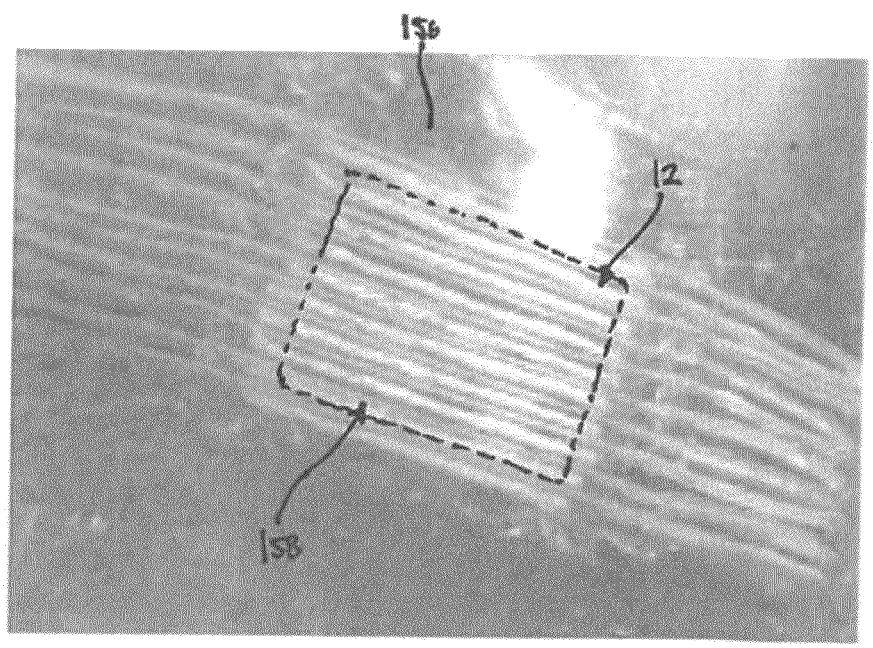
Figure 12F:
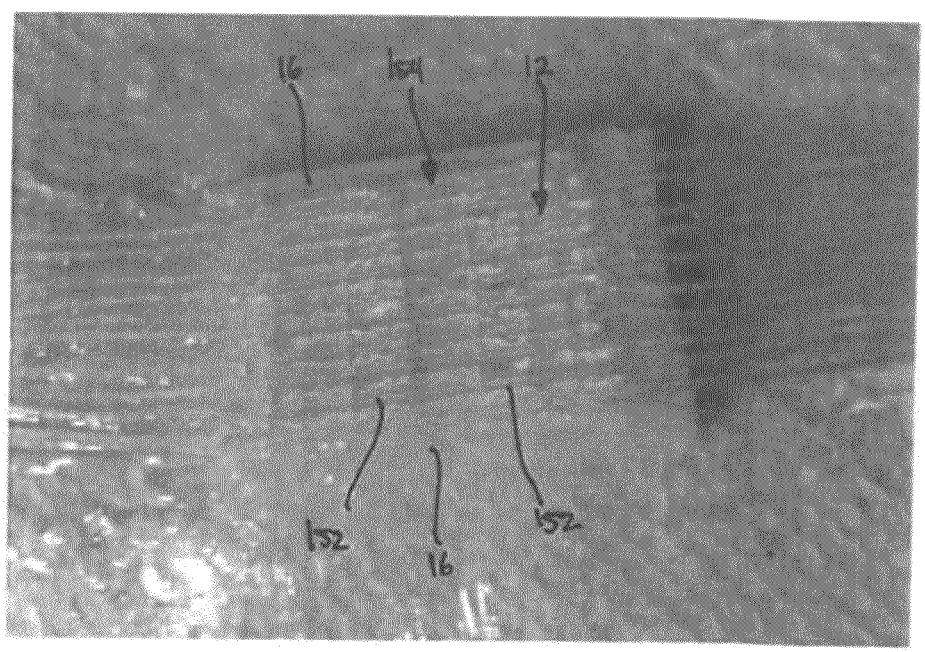
Figure 12G:
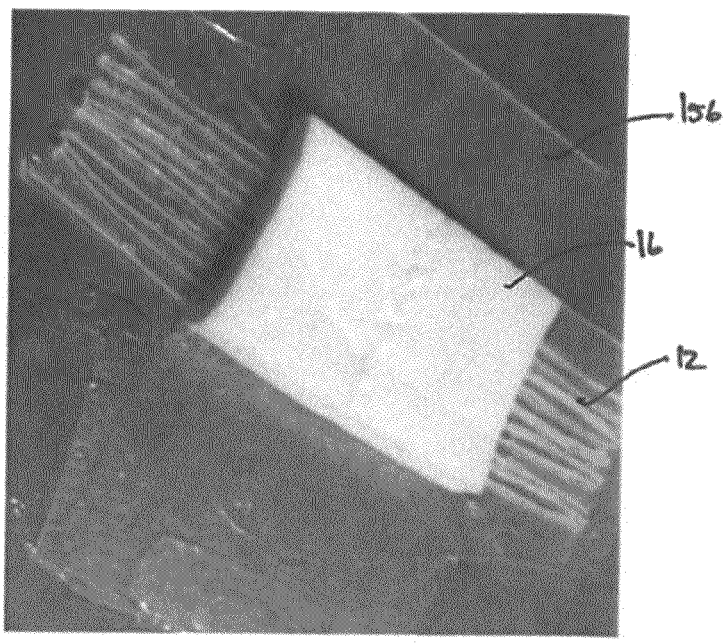

The fiber array may then have an oxygen permeable film 156, e.g., silicone film which may be temporarily backed by polyethylene for handling, may be aligned with the fiber array such that an open area 158 formed in the film 156 is aligned with the fiber array, as shown in the perspective view of FIG. 12E. The fiber array may be adhered to the film 156 with an adhesive such that the adhesive stripes 152 face away from the open area 158 of film 156. The hydrophilic absorbent material 16 may then be laid atop the fiber array and film 156 and optionally secured with an adhesive, as shown in the respective bottom and top views of FIGS. 12F and 12G.

Figure 12H:
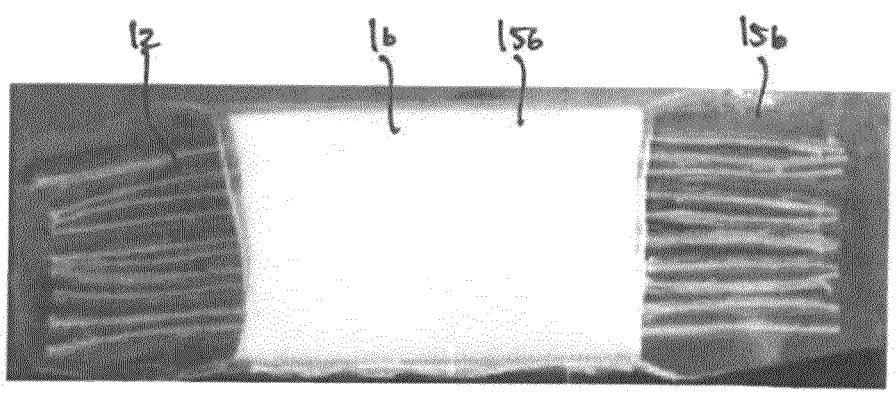
Figure 12I:
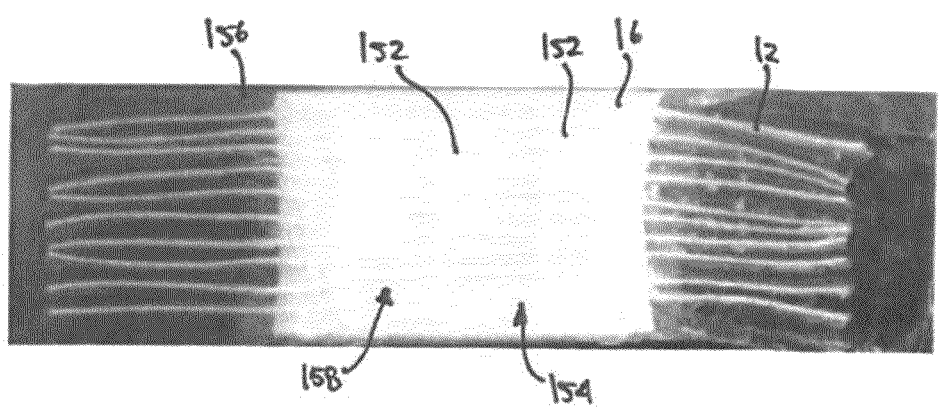
Figure 12J:
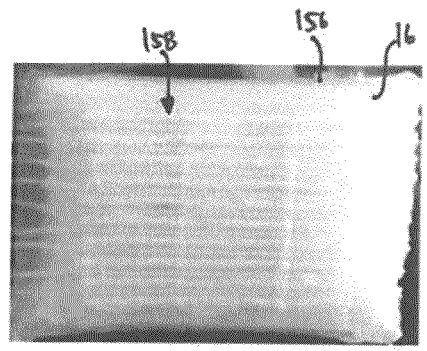
Figure 12K:
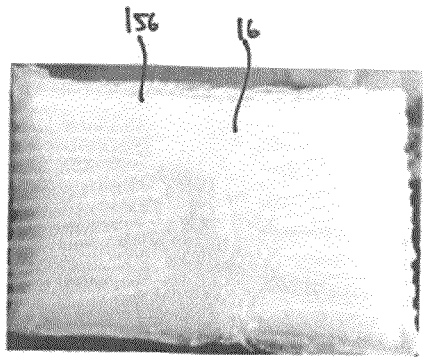

With the fiber array and foam so arranged, the film 156 may be wrapped to cover and completely envelope the assembly while leaving the fiber array exposed within the open area 158 for contacting the wound, keeping the ends accessible to an oxygen reservoir as shown in the respective top and bottom views of FIGS. 12H and 12I. The exposed terminal ends of the fibers may be optionally wrapped over the top portion of the hydrophilic absorbent material 16, if desired, and secured (e.g., via RTV paste) as shown in respective bottom and top views of FIGS. 12J and 12K.

Figure 12L:
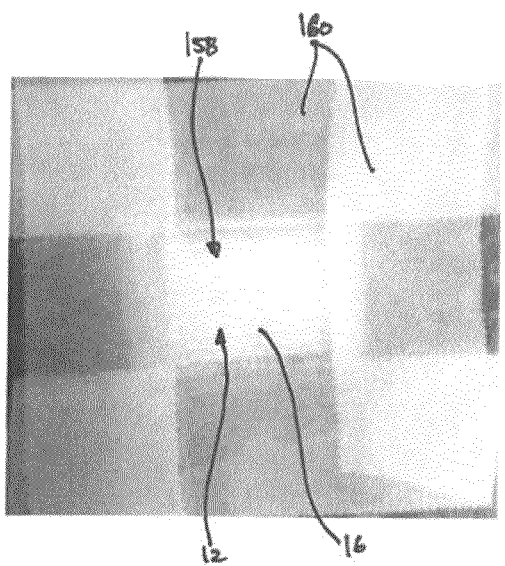
Figure 12M:
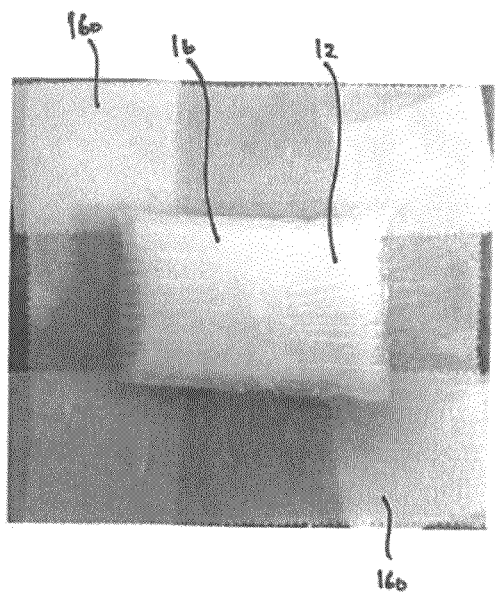
Figure 12N:
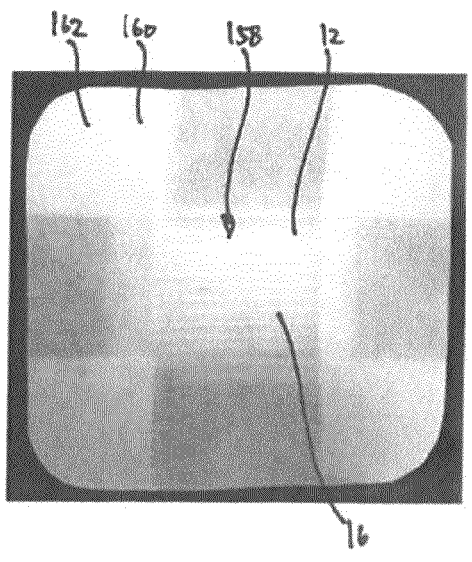
Figure 12O:
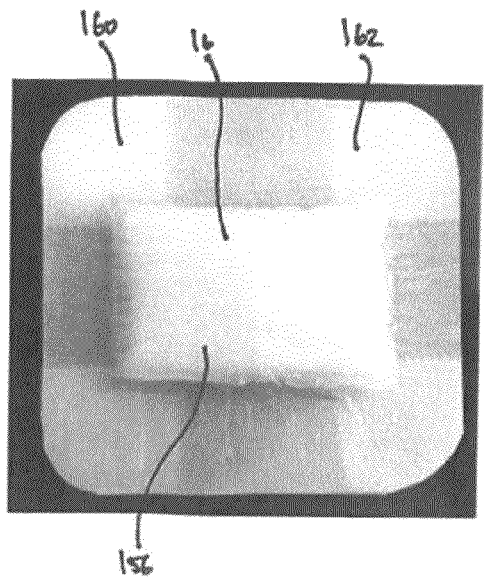
Figure 12P:
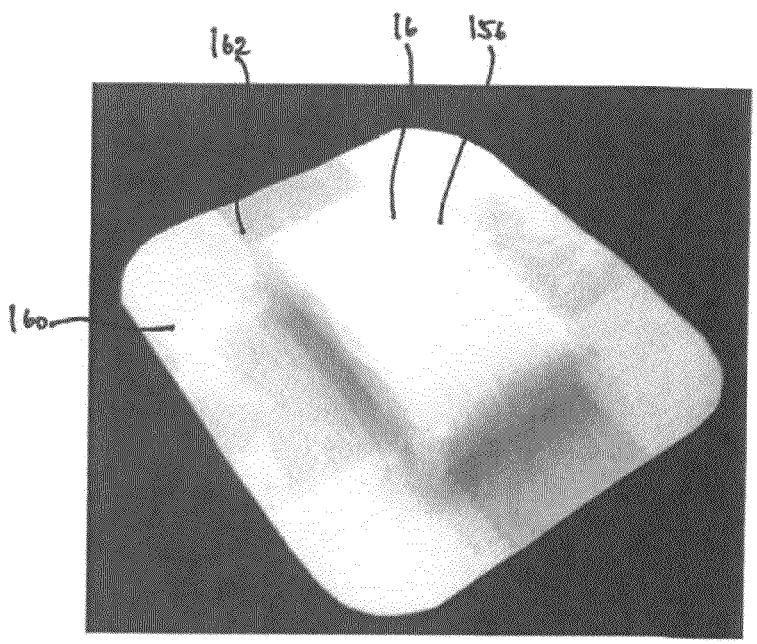

To complete the wound dressing, a frame of adhesive tape 160, e.g., medical adhesive tape, may be arranged around the fiber array and hydrophilic absorbent material so as to leave the open area 158 exposed for contact against the wound. FIGS. 12L and 12M show bottom and top views of an example where the adhesive tape 160 may be arranged about the assembly. The fiber array and hydrophilic absorbent material assembly may be adhered to or otherwise secured to the tape, which may be trimmed to form border 162, as shown in the respective bottom, top, and perspective views of FIGS. 12N-12P. The border 162 may thus allow for the dressing to be secured over a wound such that the exposed fibers 12, 52 along open area 158 directly contact the wound while border 162 prohibits or inhibits any exudate from wicking laterally along the dressing.

Figure 13A:
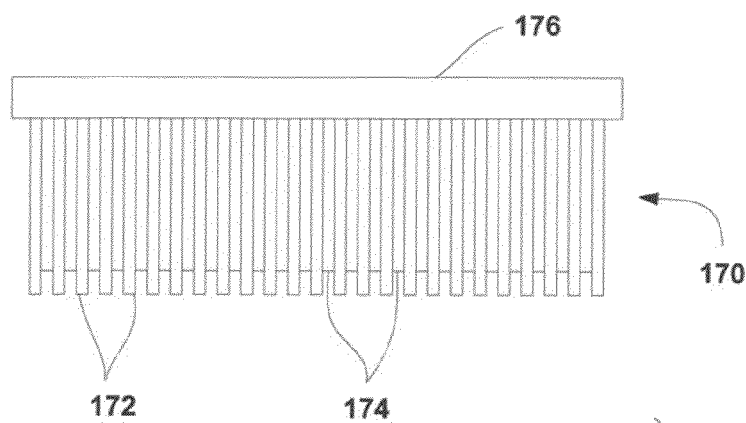
FIG. 13A illustrates an example of an array having members of alternating length for forming oxygen conduits.
Figure 13B:
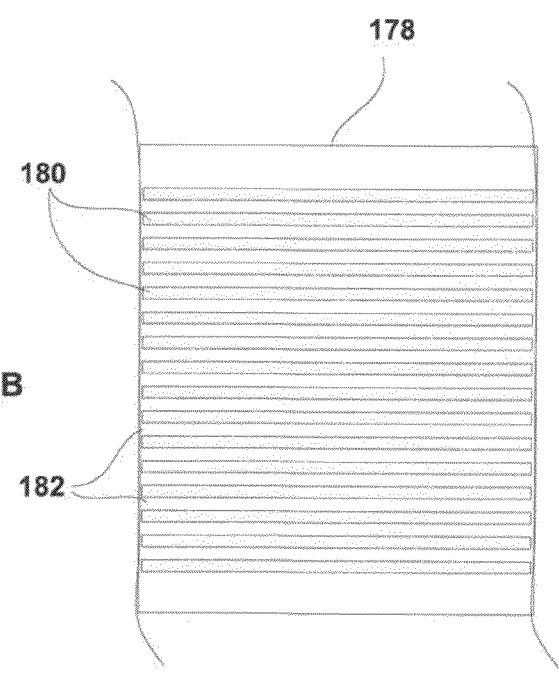
FIGS. 13B and 13C illustrate top views of oxygen conduits which may be formed utilizing the array of FIG. 13A.
Figure 13C:
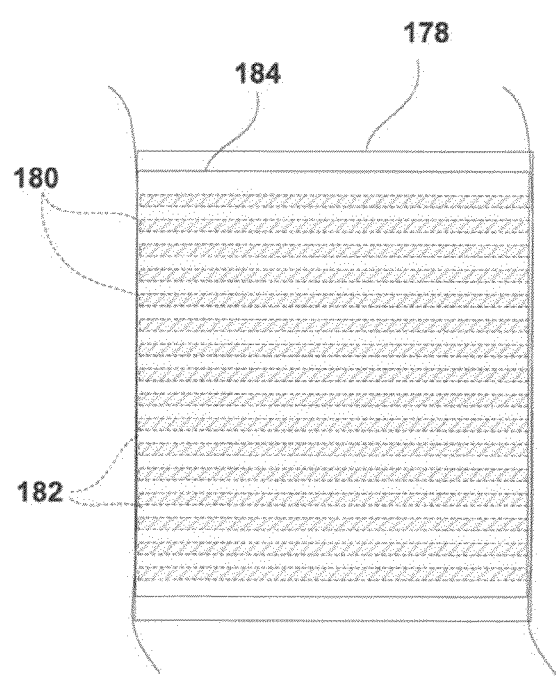

Yet another variation for manufacturing a fiber array assembly is shown in FIGS. 13A to 13C. In this variation, an array 170 of tines or elongate members may be used to comb or rake a thin layer of any of the oxygen diffusive materials described herein, such as RTV silicone paste, onto a cured silicone film. Such an array 170 may generally comprise a base 176 having a first set of aligned members 172 having a first length and a second set of aligned members 174 having a second length which is shorter than the first length. Each of the members 172, 174 may be alternated such that regions may be framed between the members 172 and 174, as shown in FIG. 13A. The difference between the lengths of 172 and 174 may form the barriers between each adjacent oxygen diffusive channel.

A layer of the silicone paste may be laid upon the cured silicone film 178 and array 170 may be combed or raked over the film such that parallel channels 182 (where members 172 are raked) are formed between silicone barriers 180 (where members 174 are raked), as shown in FIG. 13B. A second thin film of silicone 184 may be laid upon the raked silicone paste prior to curing such that the channels 182 are enclosed and separated between films 178, 184 and silicone barriers 180, as shown in FIG. 13C.

Once the silicone has cured, the array may be cut or otherwise separated longitudinally between every few channels 182 to produce relatively thinner multi-lumen ribbons. The separated ribbons may be attached to adhered to one another (e.g., via bonding with orthogonally positioned silicone strips, as described herein) to form a composite fiber array such as the variation shown above in FIG. 8. An example is shown in the FIG. 14A which illustrates a fiber array which has been formed and cured and then cut longitudinally into individual sub-assemblies 121A, 121B, 121C, 121D. Although four sub-assemblies are shown, any number of sub-assemblies may be formed as desired. Each of the sub-assemblies may have one or several oxygen conduits formed through the ribbons.

Each of the sub-assemblies 121A, 121B, 121C, 121D may be aligned with respect to one another to form a composite fiber array 190 having longitudinally aligned gaps, spaces, or channels 196 between each adjacent sub-assembly, as shown in FIG. 14B. The composite fiber array 190 may then be either adhered directly to one another (e.g., via orthogonally aligned silicone adhesive, as described herein) and/or directly to another substrate such as a hydrophobic absorbent material 194 such as gauze, sponge, etc. Each of the oxygen conduits may be optionally filled at least partially with silicone to seal the channels to prevent or inhibit any exudate from wicking laterally through the channels.

FIG. 14C shows a top view of the absorbent material 194 having the composite fiber array 190 attached on the opposing side. A hydrophilic absorbent material may also be placed or situated along one or portions of the gaps or channels 196 to facilitate exudate wicking from the wound surface to the absorbent material 194. For instance, one or more absorbent threads (such as cotton threads) may be aligned longitudinally along the gaps or channels 196 between adjacent sub-assemblies 121A, 121B, 121C, 121D.

The oxygen channels of the composite fiber array 190 may be formed in any of the variations described above, if desired. For instance, fibers may be placed along each of the channels or the channels may be alternated with hydrophilic materials as well, as previously described.

Figure 14D:
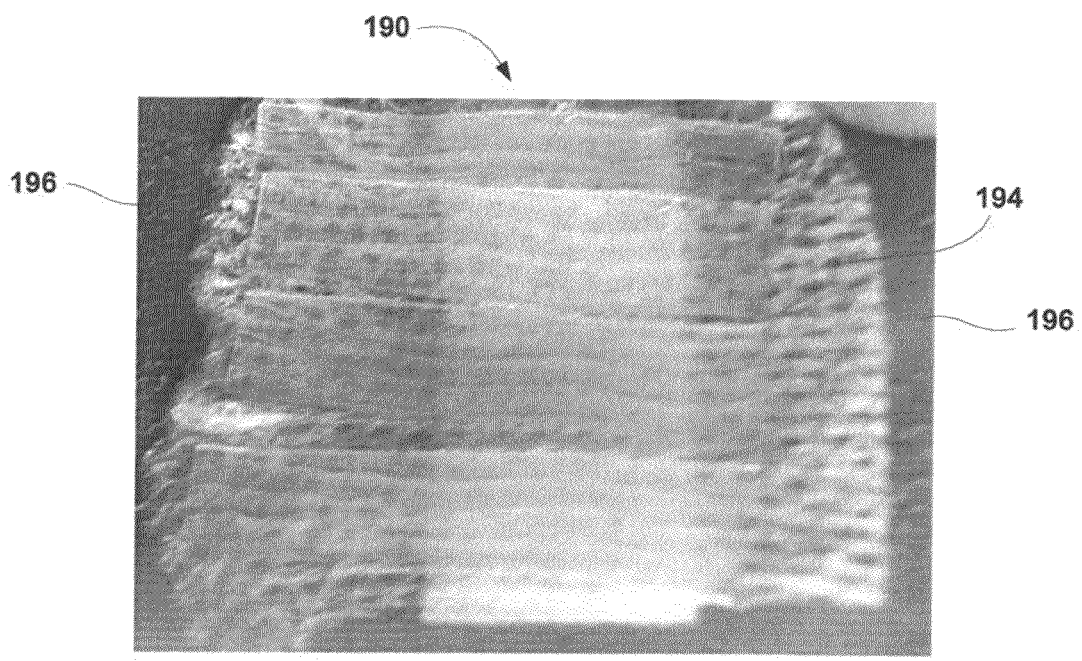
FIGS. 14D and 14E illustrate alternative variations for utilizing a composite fiber array with various dressings.
Figure 14E:
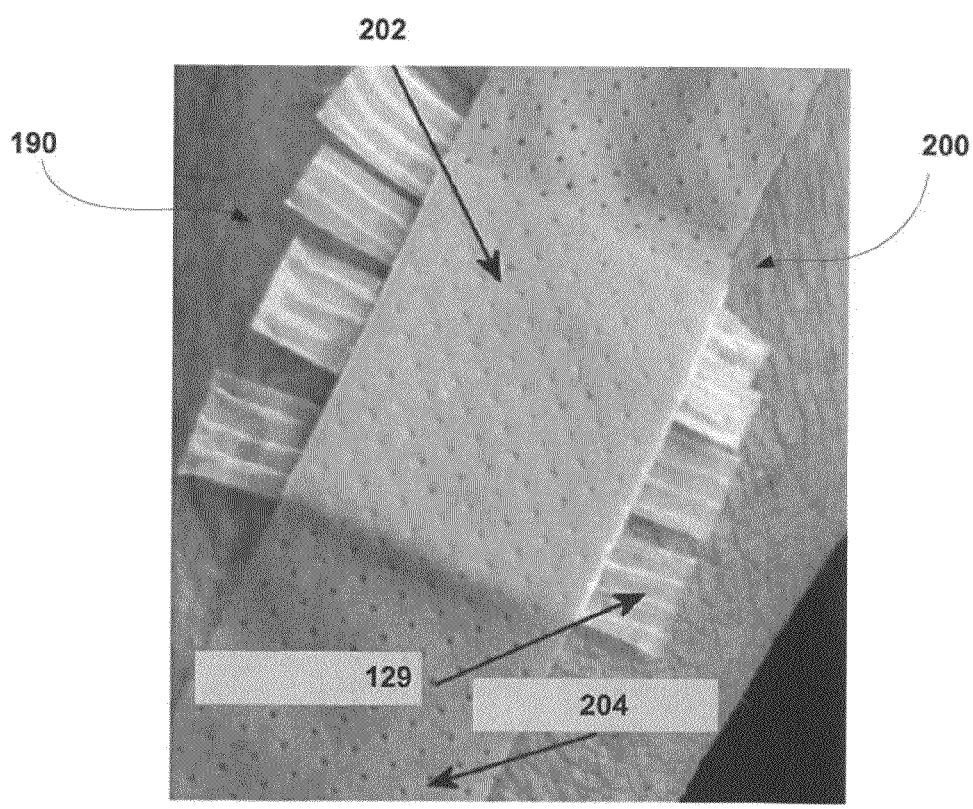

With the composite fiber array 190 formed, it may be applied directly upon the wound for treatment. Alternatively, the fiber array 190 may be adhered or placed upon an adhesive border 196, as shown in FIG. 14D. In yet another variation, the composite fiber array 190 may be used without any hydrophilic absorbent material for application directly upon a wound surface. In yet another variation, the composite fiber array 190 may be used in conjunction with a conventional dressing such as an adhesive bandage 200. The composite fiber array 190 may be placed directly into contact against a wound surface between the gauze 202 of adhesive bandage 200, as shown in FIG. 14E. The oxygen antenna 129 may be placed to extend beyond the bandage to ensure oxygen absorption and diffusion through the channels while the assembly may be held against the wound surface via the adhesive 204 of bandage 200.

The apparatus and methods disclosed above are not limited to the individual embodiments which are shown or described but may include combinations to wound dressings which incorporate individual features between the different variations. Modification of the above-described assemblies and methods for carrying out the invention, combinations between different variations as practicable, and variations of aspects of the invention that are obvious to those of skill in the art are intended to be within the scope of the claims.

What is claimed is:

1. A wound dressing, comprising:
   a hydrophilic absorbent material;
   a hydrophilic absorbent material envelope which defines an open area for contacting a wound site and which at least partially encloses the hydrophilic absorbent material; and
   at least one conduit having an oxygen-diffusive coating and a lumen which allows diffusion of oxygen or oxygenated fluid along its length,
   wherein at least one area of the conduit is positioned to extend exposed along the open area in contact with the wound site and adjacent to the hydrophilic absorbent material such that the wound site and hydrophilic absorbent material are in fluid communication, and wherein the at least one conduit has at least one portion further exposed to ambient air.

2. The dressing of claim 1 wherein the hydrophilic absorbent material envelope impedes water vapor transmission.

3. The dressing of claim 1 further comprising at least one multifilament fiber positioned through the at least one conduit.

4. The dressing of claim 1 further comprising at least one hydrophilic element interspersed with the at least one conduit.

5. The dressing of claim 1 wherein the hydrophilic absorbent material is removable and/or replaceable from the hydrophilic absorbent material envelope.

6. The dressing of claim 1 wherein the at least one conduit comprises a diameter range from 40 to 2000 micron.

7. The dressing of claim 6 wherein the at least one conduit comprises a diameter range from 80 to 260 micron.

8. The dressing of claim 1 wherein the oxygen-diffusive coating has a thickness of about 50 to 300 micron.

9. The dressing of claim 1 wherein the oxygen-diffusive coating is comprised of silicone.

10. The dressing of claim 1 wherein the oxygen-diffusive coating defines one or more micro-perforations which are sized to exclude aqueous fluid permeation via surface tension effects.

11. The dressing of claim 1 wherein the oxygen-diffusive coating has an external surface which is modified to be hydrophilic.

12. The dressing of claim 1 wherein the hydrophilic absorbent material envelope comprises an oxygen permeable material.

13. The dressing of claim 1 further comprising an access port upon the hydrophilic absorbent material envelope which is in fluid communication with the hydrophilic absorbent material.

14. The dressing of claim 13 further comprising a vacuum apparatus fluidly coupled to the access port for removing exudate from the wound dressing.

15. The dressing of claim 13 wherein the access port can be reversibly opened to permit evaporation of water from the hydrophilic absorbent material.

16. The dressing of claim 1 further comprising an adhesive border formed around a periphery of the wound dressing.

17. The dressing of claim 1 further comprising a drug, medicant or agent infused into the hydrophilic absorbent material.

18. The dressing of claim 1 further comprising a plurality of additional conduits each having an oxygen-diffusive coating.

19. The dressing of claim 18 wherein the plurality of additional conduits are formed transversely relative to one another.

20. The dressing of claim 18 further comprising one or more oxygen permeable adhesive stripes formed transversely relative to lengths of the conduits.

21. The dressing of claim 1 further comprising a perforated or semi-permeable membrane over the open area for contacting the wound site.

22. The dressing of claim 21 further comprising one or more channels formed through the perforated or semi-permeable membrane and positioned to fluidly couple the wound site and the hydrophilic absorbent material.

23. The dressing of claim 21 wherein the perforated or semi-permeable membrane defines one or more ridges or notches to form the at least one conduit.

24. The dressing of claim 1 further comprising a pump in fluid communication with the at least one conduit.

25. The dressing of claim 1 wherein the dressing further comprises an agent that is adapted to be applied to the wound site, wherein the agent is selected from the group consisting of platelet gel, plasma concentrate, white cells, stem cells, skin grafts, and growth factors.

26. A wound dressing, comprising:
a hydrophilic absorbent material;
at least one conduit having an oxygen-diffusive coating and a lumen which allows diffusion of oxygen or oxygenated fluid along its length,
wherein at least one area of the conduit is positioned to extend in contact with a wound surface and adjacent to the hydrophilic absorbent material such that the wound surface and hydrophilic absorbent material are in fluid communication, and wherein the at least one conduit has at least one portion further exposed to ambient air.

27. The dressing of claim 26 further comprising a hydrophilic absorbent material envelope which defines an open area for contacting the wound surface and which at least partially encloses the hydrophilic absorbent material, wherein the at least one area of the conduit is exposed along the open area for contact with the wound surface.

28. The dressing of claim 27 wherein the hydrophilic absorbent material envelope impedes water vapor transmission.

29. The dressing of claim 27 wherein the hydrophilic absorbent material is removable and/or replaceable from the hydrophilic absorbent material envelope.

30. The dressing of claim 27 wherein the hydrophilic absorbent material envelope comprises an oxygen permeable material.

31. The dressing of claim 27 further comprising an access port upon the hydrophilic absorbent material envelope which is in fluid communication with the hydrophilic absorbent material.

32. The dressing of claim 31 further comprising a vacuum apparatus fluidly coupled to the access port for removing exudate from the wound dressing.

33. The dressing of claim 31 wherein the access port can be reversibly opened to permit evaporation of water from the hydrophilic absorbent material.

34. The dressing of claim 27 further comprising a perforated or semi-permeable membrane over the open are for contacting the wound surface.

35. The dressing of claim 34 farther comprising one or more channels formed through the perforated or semi-permeable membrane and positioned to fluidly couple the wound surface and the hydrophilic absorbent material.

36. The dressing of claim 34 wherein the perforated or semi-permeable membrane defines one or more ridges or notches which also form the at least one conduit.

37. The dressing of claim 26 further comprising at least one multifilament fiber positioned through the at least one conduit.

38. The dressing of claim 26 further comprising at least one hydrophilic element interspersed with the at least one conduit.

39. The dressing of claim 26 wherein the at least one conduit comprises a diameter range from 40 to 2000 micron.

40. The dressing of claim 39 wherein the at least one conduit comprises a diameter range from 80 to 260 micron.

41. The dressing of claim 26 wherein the oxygen-diffusive coating has a thickness of about 50 to 300 micron.

42. The dressing of claim 26 wherein the oxygen-diffusive coating is comprised of silicone.

43. The dressing of claim 26 wherein the oxygen-diffusive coating defines one or more micro-perforations which are sized to exclude aqueous fluid permeation via surface tension effects.

44. The dressing of claim 26 wherein the oxygen-diffusive coating has an external surface which is modified to be hydrophilic.

45. The dressing of claim 26 further comprising an adhesive border formed around a periphery of the wound dressing.

46. The dressing of claim 26 further comprising a drug, medicant or agent infused into the hydrophilic absorbent material.

47. The dressing of claim 26 further comprising a plurality of additional conduits each having an oxygen-diffusive coating.

48. The dressing of claim 47 wherein the plurality of additional conduits are formed transversely relative to one another.

49. The dressing of claim 47 further comprising one or more oxygen permeable adhesive stripes formed transversely relative to lengths of the conduits.

50. The dressing of claim 26 further comprising a pump in fluid communication with the at least one conduit.

51. The dressing of claim 26 wherein the dressing further comprises an agent that is adapted to be applied to the wound surface, wherein the agent is selected from the group consisting of platelet gel, plasma concentrate, white cells, stem cells, skin grafts, and growth factors.

52. A wound dressing, comprising:
a hydrophilic absorbent material;
at least one oxygen conductive hydrophobic conduit extending therethrough or adjacent therealong of the wound dressing; and
a hydrophilic absorbent material envelope which defines an open area for contacting a wound site and which at least partially encloses the hydrophilic absorbent material,
wherein at least a portion of the at least one oxygen conductive hydrophobic conduit is positioned to extend exposed along the open area in contact with the wound site and adjacent to the hydrophilic absorbent material such that the wound site and hydrophilic absorbent material are in fluid communication; and
wherein at least one area or the at least one oxygen conductive hydrophobic conduit is in contact with ambient air and is permeable to oxygen.

53. The dressing of claim 52 further comprising at least one multifilament fiber positioned through the at least one oxygen conductive hydrophobic conduit.

54. The dressing of claim 52 further comprising at least one hydrophilic element interspersed with the at least one oxygen conductive hydrophobic conduit.

55. The dressing of claim 52 wherein the hydrophilic absorbent material is removable and/or replaceable from the hydrophilic absorbent material envelope.

56. The dressing of claim 52 wherein the at least one oxygen conductive hydrophobic conduit comprises a diameter range from 40 to 2000 micron.

57. The dressing of claim 56, wherein the at least one oxygen conductive hydrophobic conduit comprises a diameter range from 80 to 260 micron.

58. The dressing of claim 52 wherein the oxygen conductive hydrophobic conduit has a thickness of about 50 to 300 micron.

59. The dressing of claim 52 wherein the oxygen conductive hydrophobic conduit is comprised of silicone.

60. The dressing of claim 52 wherein the oxygen conductive hydrophobic conduit defines one or more micro-perforations which are sized to exclude aqueous fluid permeation via surface tension effects.

61. The dressing of claim 52 wherein the oxygen conductive hydrophobic conduit has an oxygen-diffusive coating having and external surface which is modified to be hydrophilic.

62. The dressing of claim 52 wherein the hydrophilic absorbent material envelope comprises an oxygen permeable material.

63. The dressing of claim 52 further comprising an access port upon the hydrophilic absorbent material envelope which is in fluid communication with the hydrophilic absorbent material.

64. The dressing of claim 63 further comprising a vacuum apparatus fluidly coupled to the access port for removing exudate from the wound dressing.

65. The dressing of claim 52 further comprising an adhesive border formed around a periphery of the wound dressing.

66. The dressing of claim 52 further comprising a drug, medicant or agent infused into the hydrophilic absorbent material.

67. The dressing of claim 52 further comprising a plurality of additional conduits each having an oxygen-diffusive covering.

68. The dressing of claim 67 wherein the plurality of additional conduits are formed transversely relative to one another.

69. The dressing of claim 67 further comprising one or more oxygen permeable adhesive stripes formed transversely relative to lengths of the conduits.

70. The dressing of claim 52 further comprising a perforated or semi-permeable membrane over the open area for contacting the wound site.

71. The dressing of claim 70 further comprising one or more channels formed through the perforated or semi-permeable membrane and positioned to fluidly couple the wound site and the hydrophilic absorbent material.

72. The dressing of claim 70 wherein the perforated or semi-permeable membrane also defines one or more ridges or notches to form the at least one conduit.

73. The dressing of claim 52 further comprising a pump in fluid communication with the at least one conduit.

74. The dressing of claim 52 wherein the dressing further comprises an agent that is adapted to be applied to the wound site, wherein the agent is selected from the group consisting of platelet gel, plasma concentrate, white cells, stem cells, skin grafts, and growth factors.

75. A wound dressing, comprising:
at least one conduit having an oxygen-diffusive coating and a lumen which allows diffusion of oxygen or oxygenated fluid along its length, wherein the at least one conduit defines a wound contact region for contact with a wound surface and an oxygen absorption region which is configured to extend beyond the wound surface and is exposed to ambient air; and
an adhesive border formed around a periphery of the wound dressing.

76. The dressing of claim 75 further comprising:
a hydrophilic absorbent material which is in fluid communication with the wound surface; and
a hydrophilic absorbent material envelope which defines an open area for contacting the wound surface and which at least partially encloses the hydrophilic absorbent material.

77. The dressing of claim 76 wherein the hydrophilic absorbent material envelope impedes water vapor transmission.

78. The dressing of claim 76 wherein the hydrophilic absorbent material is removable and/or replaceable from the hydrophilic absorbent material envelope.

79. The dressing of claim 75 wherein the oxygen-diffusive coating is comprised of silicone.

80. The dressing of claim 75 wherein the at least one conduit extends through the adhesive border.

81. A method of treating a wound, comprising:
providing a wound dressing having a hydrophilic absorbent material, a hydrophilic absorbent material envelope which defines an open area for contacting a wound site and which at least partially encloses the hydrophilic absorbent material, and at least one conduit having an oxygen-diffusive coating;
placing the open area upon the wound site such that the at least one conduit is in contact against the wound site and the wound site and hydrophilic absorbent material are in fluid communication; and diffusing oxygen from the at least one conduit and through the oxygen-diffusive coating to the wound site.

82. The method of claim 81 wherein the at least one conduit is positioned to extend exposed along the open area and adjacent to the hydrophilic absorbent material.

83. The method of claim 81 further wicking exudate from the wound site to the hydrophilic absorbent material.

84. The method of claim 81 wherein placing the open area upon the wound site comprises maintaining a separation between the hydrophilic absorbent material and the wound site.

85. The method of claim 81 wherein the at least one conduit comprises at least one coated multifilament fiber positioned through the at least one conduit.

86. The method of claim 85 wherein prior to providing a wound dressing, permeating the multifilament fiber with a fluid to transiently obstruct open inter-filament spaces before applying the oxygen diffusive coating.

87. The method of claim 81 wherein the wound dressing further comprises at least one hydrophilic element interspersed with the at least one conduit.

88. The method of claim 81 wherein the oxygen-diffusive coating is comprised of silicone.

89. The method of claim 81 further removing excess exudate from the wound site via an access port upon the hydrophilic absorbent material envelope which is in fluid communication with the hydrophilic absorbent material.

90. The method of claim 89 wherein removing excess exudate comprises suctioning the exudate from the wound site.

91. The method of claim 81 wherein placing the open area upon the wound site comprises adhering the wound dressing around a periphery of the wound site via an adhesive border.

92. The method of claim 81 further comprising infusing a drug, medicant or agent into the hydrophilic absorbent material.

93. The method of claim 81 further comprising inhibiting evaporation from the hydrophilic absorbent material via the hydrophilic absorbent material envelope.

94. The method of claim 81 comprising an oxygen delivery system comprising pumping an oxygen-rich fluid through the at least one conduit via a pump or pressurized reservoir.

95. The method of claim 81 further comprising applying a treatment to the wound site selected from the group consisting of platelet gel, plasma concentrate, white cells, stem cells, skin grafts, and growth factors.

96. The method of claim 95 wherein the treatment is applied prior to, during, or after placing the open area upon the wound site.

97. The method of claim 81 further comprising removing the hydrophilic absorbent material from the hydrophilic absorbent material envelope.

98. The method of claim 97 wherein the hydrophilic absorbent material is removed from the hydrophilic absorbent material envelope while maintaining the open area upon the wound site.

* * * * *